United States Patent
Lizarzaburu Chavez et al.

(10) Patent No.: US 12,262,670 B2
(45) Date of Patent: *Apr. 1, 2025

(54) ToLCNDV RESISTANT MELON PLANTS

(71) Applicant: NUNHEMS B.V., Nunhem (NL)

(72) Inventors: Juan Antonio Lizarzaburu Chavez, Sta. Maria del Aguila (ES); Jeffrey Skoneczka, Davis, CA (US); Daniel Bellon Dona, La Parma-Cartagena (ES)

(73) Assignee: NUNHEMS B.V., Nunhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,372

(22) Filed: Oct. 24, 2023

(65) Prior Publication Data

US 2024/0122144 A1     Apr. 18, 2024

Related U.S. Application Data

(60) Continuation of application No. 17/307,169, filed on May 4, 2021, now Pat. No. 11,832,572, which is a division of application No. 16/606,979, filed as application No. PCT/EP2018/060067 on Apr. 19, 2018, now Pat. No. 11,111,502.

(60) Provisional application No. 62/500,948, filed on May 3, 2017.

(30) Foreign Application Priority Data

Apr. 21, 2017   (EP) ..................... 17167580

(51) Int. Cl.
*A01H 6/34*    (2018.01)
*A01H 1/04*    (2006.01)
*A01H 5/08*    (2018.01)
*C12N 15/82*   (2006.01)

(52) U.S. Cl.
CPC ............. *A01H 6/344* (2018.05); *A01H 1/045* (2021.01); *A01H 5/08* (2013.01); *C12N 15/8283* (2013.01)

(58) Field of Classification Search
CPC .................................................. A01H 6/344
See application file for complete search history.

(56) References Cited

U.S. PATENT DOCUMENTS 11,111,502 B2 *  9/2021  Lizarzaburu Chavez .................. C12N 15/8283

FOREIGN PATENT DOCUMENTS

EP    3187040 A1     7/2017
WO    2017114848 A1  7/2017

OTHER PUBLICATIONS

"Guidelines for the conduct of tests for Distinctness, Uniformity and Stability, UPOV Code: CUCUM_MEL", International Union for the protection of New Varieties of Plants, TG/104/5, 2006, 69 pages.
Allen, et al., "Transcript-specific, single-nucleotide polymorphism discovery and linkage analysis in hexaploid bread wheat (*Triticum aestivum* L.)", Plant Biotechnology Journal, vol. 9, Issue 9, Dec. 2011, pp. 1086-1099.
Burger, et al., "Development of Sweet Melon (*Cucumis melo*) Genotypes Combining High Sucrose and Organic Acid Content", Journal of the American Society for Horticultural Science, vol. 128, Issue 4, Jul. 2003, pp. 537-540.
Diaz, et al., "Anchoring the consensus ICuGI genetic map to the melon (*Cucumis melo* L.) genome", Molecular Breeding, vol. 35, Issue 188, Sep. 22, 2015, pp. 1-7.
European Search Report for EP Patent Application No. 17167580.4, Issued on Jan. 2, 2018, 4 pages.
Gur, et al., "Genome-Wide Linkage-Disequilibrium Mapping to the Candidate Gene Level in Melon (*Cucumis melo*)", Scientific Reports, vol. 7, 2017, 13 pages.
Henikoff, et al., "Amino acid substitution matrices from protein blocks", Journal Proceedings of the National Academy of Sciences of the United States of America, vol. 89, Issue 22, Nov. 15, 1992, pp. 10915-10919.
International Search Report for PCT Patent Application No. PCT/EP2018/060067, Issued on Jul. 19, 2018, 6 pages.
Islam, et al., "Genetics of resistance in Luffa cylindrica Roem. against Tomato leaf curl New Delhi virus", Euphytica, vol. 174, Issue 1, Feb. 2010, pp. 83-89.
Lin, et al., "Genomic analyses provide insights into the history of tomato breeding", Nature Genetics, vol. 46, Issue 11, Oct. 12, 2014, pp. 1220-1226.
Lopez, et al., "Mechanical transmission of Tomato leaf curl New Delhi virus to cucurbit germplasm: selection of tolerance sources in Cucumis melo", Euphytica, vol. 204, Issue 3, Jan. 28, 2015, pp. 679-691.
Saez, et al., "Inheritance of tolerance to Tomato leaf curl New Delhi virus (ToLCNDV) in melon [Conference poster]", Cucurbitaceae 2016, XIth Eucarpia Meeting on Cucurbit Genetics & Breeding, Jul. 24-28, 2016, pp. 214-216.
Saez, et al., "Resistance to Tomato leaf curl New Delhi virus in Cucurbita spp.", Annals of Applied Biology, vol. 169, Issue 1, Mar. 16, 2016, pp. 91-105.
Saez, et al., "Resistance to tomato leaf curl New Delhi virus in melon is controlled by a major QTL located in chromosome 11", Plant Cell Reports, vol. 36, Issue 10, Jul. 14, 2017, pp. 1571-1584.
Simon, et al., "Absolute Quantification of Tomato leaf curl New Delhi virus Spain strain, ToLCNDV-ES: Virus Accumulation in a Host-Specific Manner", Plant Disease, vol. 102, Issue 1, Jan. 2018, pp. 165-171.
Varma, et al., "GE Tomato Resistant to leaf Curl Disease", ISB News Report, Jun. 2006, 3 pages.

* cited by examiner

*Primary Examiner* — Brent T Page
(74) *Attorney, Agent, or Firm* — ArentFox Schiff LLP

(57) ABSTRACT

The present invention relates to ToLCNDV resistant melon plants comprising one or two introgression fragments in their genome.

14 Claims, 1 Drawing Sheet
Specification includes a Sequence Listing.

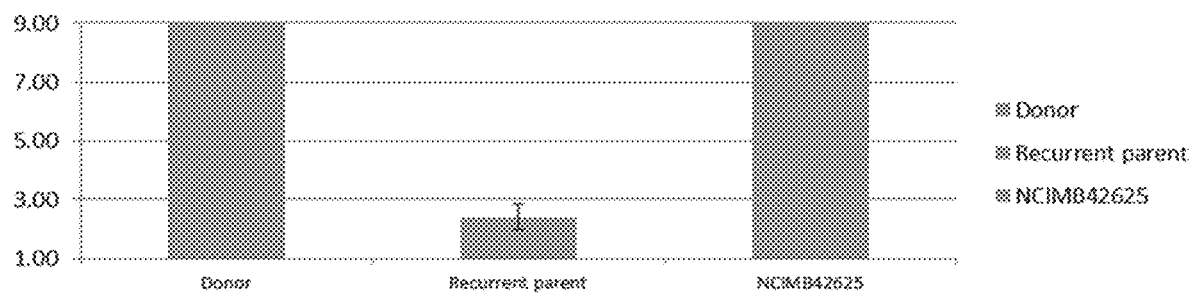

SEQUENCE LISTING

```
Sequence total quantity: 28
SEQ ID NO: 1            moltype = DNA  length = 201
FEATURE                 Location/Qualifiers
source                  1..201
                        mol_type = genomic DNA
                        organism = Cucumis melo
SEQUENCE: 1
gctaatgaac tcgggttttg aaacgctcag aggattatcg ttaccggaaa catgaacgga  60
agtccatgtt ttgacaaacg aactaatgga cgacgcgtcg aaaatcttgt gcgacatgag  120
taagccaaca gtaatgcctc cacattgaaa cgtcgtggtt tggatgagta caatacatcc  180
tttgttagcg agatgaaaag g                                            201

SEQ ID NO: 2            moltype = DNA  length = 201
FEATURE                 Location/Qualifiers
source                  1..201
                        mol_type = genomic DNA
                        organism = Cucumis melo
SEQUENCE: 2
gtttgttttg atcaaaaaaa tcaaacattt aagtaaataa tatactacat taaatgtgta  60
agtgagtcta gcagtataca ttccgtcgat gtactaaact gaattcaaag agtttatgca  120
tataagtgaa tgaatatccc aaaacttatc aatttcagaa gaagagaaaa aactaggttt  180
ccttatcctt tttgtgagcc a                                            201
```

SEQ ID NO: 3          moltype = DNA  length = 201
FEATURE               Location/Qualifiers
source                1..201
                      mol_type = genomic DNA
                      organism = Cucumis melo
SEQUENCE: 3
ctcgtagagc atttgaacgc cacagtggaa ctggccgtgg gtaagtgtct gctgtctgtt    60
cttttaaatt ttgttgtgca cactcctgct gcatattcta tgccattttg acacttcatt   120
cctgatttta tgcctagaaa tgaatttaaa cgagaagggt ctggtcgtgg aaattgggga   180
aggtcaactg acgaatttgc t                                             201

SEQ ID NO: 4          moltype = DNA  length = 201
FEATURE               Location/Qualifiers
source                1..201
                      mol_type = genomic DNA
                      organism = Cucumis melo
SEQUENCE: 4
tctctctggt ggataactca tgtaatggtc ttgtctttat ttgtaagtgt gcttttttta    60
ctcgttgtga tggcatattc aatcctatga ctaatgagtt tttccaaatt cctcgaggtg   120
aattagatgt tgatatttac tcctacgaat taggttttag ccctacaaca aagcaataca   180
aattgtttcg agttaccgaa t                                             201

SEQ ID NO: 5          moltype = DNA  length = 201
FEATURE               Location/Qualifiers
source                1..201
                      mol_type = genomic DNA
                      organism = Cucumis melo
SEQUENCE: 5
atacaaccca tcaaccaaaa tcttccaact aattatagag actttgataa aaggaaaaaa    60
aagagtaaca aatagcgatg cgaggaaagg gacgatggcc cgtacatatt agcatgctca   120
taaacaaatt caaaaagccc aacaaagacg aagaaaaata acgaaaacca tgatggcaca   180
aagcattgtc aagtctcgga a                                             201

SEQ ID NO: 6          moltype = DNA  length = 201
FEATURE               Location/Qualifiers
source                1..201
                      mol_type = genomic DNA
                      organism = Cucumis melo
SEQUENCE: 6
tgacaacagc tttcaccacc aatcaataaa atgaggatgg attcaagatt tatgccaaca    60
ccctgatccc aaattgaaga tgccaaacaa agggacacag gaatcattgt ctaagaaatt   120
gtaaaaaccc cacaatgaaa acttctatca aagacacggg aatctacagt ttgtacagtc   180
acttgcacaa gcatcttcaa a                                             201

SEQ ID NO: 7          moltype = DNA  length = 201
FEATURE               Location/Qualifiers
source                1..201
                      mol_type = genomic DNA
                      organism = Cucumis melo
SEQUENCE: 7
atcgttataa agtcgtcaat ggcatgacgc acaatcggtc cttcaaccat tgtaaaacca    60
acgtcgaatt tgcataacgt gtcgtcctca acatgattag tgacacgata agcgacaaaa   120
atttcggaaa aatttagttg ttgatcctca acatcgtcca cttcgggtac gtttcatata   180
cgtttatttt ggacaaccta a                                             201

SEQ ID NO: 8          moltype = DNA  length = 42
FEATURE               Location/Qualifiers
source                1..42
                      mol_type = other DNA
                      organism = synthetic construct
misc_feature          1..42
                      note = SNP_01 FAM Allele Primer
SEQUENCE: 8
gaaggtgacc aagttcatgc taactaatgg acgacgcgtc gg                      42

SEQ ID NO: 9          moltype = DNA  length = 43
FEATURE               Location/Qualifiers
source                1..43
                      mol_type = other DNA
                      organism = synthetic construct
misc_feature          1..43
                      note = SNP_01 VIC allele primer
SEQUENCE: 9
gaaggtcgga gtcaacggat tgaactaatg gacgacgcgt cga                     43

SEQ ID NO: 10         moltype = DNA  length = 26
FEATURE               Location/Qualifiers
source                1..26

```
                         mol_type = other DNA
                         organism = synthetic construct
misc_feature             1..26
                         note = SNP_01 Common Primer
SEQUENCE: 10
gttggcttac tcatgtcgca caagat                                          26

SEQ ID NO: 11            moltype = DNA  length = 53
FEATURE                  Location/Qualifiers
source                   1..53
                         mol_type = other DNA
                         organism = synthetic construct
misc_feature             1..53
                         note = SNP_02 FAM Allele Primer
SEQUENCE: 11
gaaggtgacc aagttcatgc tcattcactt atatgcataa actctttgaa ttt            53

SEQ ID NO: 12            moltype = DNA  length = 53
FEATURE                  Location/Qualifiers
source                   1..53
                         mol_type = other DNA
                         organism = synthetic construct
misc_feature             1..53
                         note = SNP_02 VIC allele primer
SEQUENCE: 12
gaaggtcgga gtcaacggat tcattcactt atatgcataa actctttgaa ttc            53

SEQ ID NO: 13            moltype = DNA  length = 29
FEATURE                  Location/Qualifiers
source                   1..29
                         mol_type = other DNA
                         organism = synthetic construct
misc_feature             1..29
                         note = SNP_02 Common Primer
SEQUENCE: 13
agcagtatac attccgtcga tgtactaaa                                       29

SEQ ID NO: 14            moltype = DNA  length = 45
FEATURE                  Location/Qualifiers
source                   1..45
                         mol_type = other DNA
                         organism = synthetic construct
misc_feature             1..45
                         note = SNP_03 FAM allele Primer
SEQUENCE: 14
gaaggtgacc aagttcatgc tcaggaatga agtgtcaaaa tggcg                     45

SEQ ID NO: 15            moltype = DNA  length = 48
FEATURE                  Location/Qualifiers
source                   1..48
                         mol_type = other DNA
                         organism = synthetic construct
misc_feature             1..48
                         note = SNP_03 VIC allele primer
SEQUENCE: 15
gaaggtcgga gtcaacggat taatcaggaa tgaagtgtca aaatggca                  48

SEQ ID NO: 16            moltype = DNA  length = 25
FEATURE                  Location/Qualifiers
source                   1..25
                         mol_type = other DNA
                         organism = synthetic construct
misc_feature             1..25
                         note = SNP_03 Common primer
SEQUENCE: 16
gtgcacactc ctgctgcata ttcta                                           25

SEQ ID NO: 17            moltype = DNA  length = 45
FEATURE                  Location/Qualifiers
source                   1..45
                         mol_type = other DNA
                         organism = synthetic construct
misc_feature             1..45
                         note = SNP_04 FAM allele primer
SEQUENCE: 17
gaaggtgacc aagttcatgc taattcacct cgaggaattt ggaag                     45

SEQ ID NO: 18            moltype = DNA  length = 47
FEATURE                  Location/Qualifiers
```

```
source                         1..47
                               mol_type = other DNA
                               organism = synthetic construct
misc_feature                   1..47
                               note = SNP_04 VIC allele primer
SEQUENCE: 18
gaaggtcgga gtcaacggat tctaattcac ctcgaggaat ttggaaa               47

SEQ ID NO: 19                  moltype = DNA  length = 30
FEATURE                        Location/Qualifiers
source                         1..30
                               mol_type = other DNA
                               organism = synthetic construct
misc_feature                   1..30
                               note = SNP_04 Common primer
SEQUENCE: 19
tggcatattc aatcctatga ctaatgagtt                                  30

SEQ ID NO: 20                  moltype = DNA  length = 52
FEATURE                        Location/Qualifiers
source                         1..52
                               mol_type = other DNA
                               organism = synthetic construct
misc_feature                   1..52
                               note = SNP_05 FAM allele primer
SEQUENCE: 20
gaaggtgacc aagttcatgc tgaatttgtt tatgagcatg ctaatatgta ca         52

SEQ ID NO: 21                  moltype = DNA  length = 51
FEATURE                        Location/Qualifiers
source                         1..51
                               mol_type = other DNA
                               organism = synthetic construct
misc_feature                   1..51
                               note = SNP_05 VIC allele primer
SEQUENCE: 21
gaaggtcgga gtcaacggat taatttgttt atgagcatgc taatatgtac g          51

SEQ ID NO: 22                  moltype = DNA  length = 22
FEATURE                        Location/Qualifiers
source                         1..22
                               mol_type = other DNA
                               organism = synthetic construct
misc_feature                   1..22
                               note = SNP_05 Common primer
SEQUENCE: 22
gcgatgcgag gaaagggacg at                                          22

SEQ ID NO: 23                  moltype = DNA  length = 52
FEATURE                        Location/Qualifiers
source                         1..52
                               mol_type = other DNA
                               organism = synthetic construct
misc_feature                   1..52
                               note = SNP_06 FAM allele primer
SEQUENCE: 23
gaaggtgacc aagttcatgc tggggttttt acaattcttt agacaatgat tt         52

SEQ ID NO: 24                  moltype = DNA  length = 51
FEATURE                        Location/Qualifiers
source                         1..51
                               mol_type = other DNA
                               organism = synthetic construct
misc_feature                   1..51
                               note = SNP_06 VIC allele primer
SEQUENCE: 24
gaaggtcgga gtcaacggat tgggttttta caatttctta gacaatgatt c          51

SEQ ID NO: 25                  moltype = DNA  length = 29
FEATURE                        Location/Qualifiers
source                         1..29
                               mol_type = other DNA
                               organism = synthetic construct
misc_feature                   1..29
                               note = SNP_06 Common primer
SEQUENCE: 25
ctgatcccaa attgaagatg ccaaacaaa                                   29

SEQ ID NO: 26                  moltype = DNA  length = 44
```

```
FEATURE              Location/Qualifiers
source               1..44
                     mol_type = other DNA
                     organism = synthetic construct
misc_feature         1..44
                     note = SNP_07 FAM allele primer
SEQUENCE: 26
gaaggtgacc aagttcatgc tgtgtcgtcc tcaacatgat tagc                          44

SEQ ID NO: 27        moltype = DNA  length = 46
FEATURE              Location/Qualifiers
source               1..46
                     mol_type = other DNA
                     organism = synthetic construct
misc_feature         1..46
                     note = SNP_07 VIC allele primer
SEQUENCE: 27
gaaggtcgga gtcaacggat tacgtgtcgt cctcaacatg attagt                        46

SEQ ID NO: 28        moltype = DNA  length = 29
FEATURE              Location/Qualifiers
source               1..29
                     mol_type = other DNA
                     organism = synthetic construct
misc_feature         1..29
                     note = SNP_07 Common primer
SEQUENCE: 28
ggacgatgtt gaggatcaac aactaaatt                                           29
```

ToLCNDV RESISTANT MELON PLANTS

CROSS-REFERENCE TO RELATED APPLICATIONS

This application is a continuation of U.S. application Ser. No. 17/307,169, filed May 4, 2021, which is divisional of U.S. application Ser. No. 16/606,979, filed Oct. 21, 2019, now U.S. Pat. No. 11,111,502, which is a National Stage Entry of PCT/EP2018/060067, filed Apr. 19, 2018, which claims priority to European Patent Application No. 17167580.4, filed Apr. 21, 2017 and U.S. Provisional Application No. 62/500,948, filed May 3, 2017, the disclosures of each of which are hereby incorporated by reference in their entireties.

REFERENCE TO AN ELECTRONIC SEQUENCE LISTING

The contents of the electronic sequence listing (039621_01125_Sequence_Listing_as_filed.xml; Size: 35,294 bytes; and Date of Creation: Oct. 10, 2023) is herein incorporated by reference in its entirety.

The application concerns cultivated melon plants (*Cucumis melo*) resistant to infection with tomato leaf curl New Dehli virus (ToLCNDV). The resistant melon plants have a genomic introgression fragment on chromosome 11 and/or on chromosome 12. The introgression fragment on chromosome 11 comprises a QTL which confers resistance to ToLCNDV in a recessive manner. The introgression fragment on chromosome 12 comprises a QTL which confers resistance to ToLCNDV in a partially dominant manner. Both QTLs together result in cultivated melon plants which show very few (average disease score of at least 8) or even no symptoms (average disease score of 9). Also disclosed are markers for identifying plants or plant parts comprising those introgression fragments and methods for identifying or producing ToLCNDV resistant melon plants.

Tomato leaf curl New Dehli virus (ToLCNDV) is classified as Begomovirus belonging to the family Geminiviridae. ToLCNDV has a bipartite genome consisting of two single stranded DNA molecules referred to as DNA A and DNA B (Saez et al., 2016, Annals of Applied Biology).

ToLCNDV was initially found to infect tomato (*Solanum lycopersicum*) plants in 1995 in India. Later ToLCNDV was found to infect also plants of other *solanacea* species, like *Solanum melongena* (aubergine), chili pepper (*Capsicum* spp.) and *Solanum tuberosum* (potato). In 2012 infection of curcubit species (courgette, *Cucurbita pepo* var. giromontiina) by ToLCNDV was found in Spain and in 2015 the virus was identified as the disease source in melon, cucumber and courgette in Tunisia. In the meantime, infection of many Curcubitacea species such as *Benincasa hispida* (wax gourd), *Citrullus lanatus* (watermelon), *Cucumis melo* (melon), *Cucumis melo* var. *flexuosus* (snake melon), *Cucumis sativus* (cucumber), *Cucurbita moschata* (musky gourd), *Cucurbita pepo* (pumpkin), *Cucurbita pepo* var. giromontiina (courgette), *Lagenaria siceraria* (bottle gourd), *Luffa cylindrica* (sponge gourd), *Momordica charantia* (bitter gourd) have been proven. Infection of weeds (e.g. *Echpta prostrata*—Asteraceae) and other crops such as *Hibiscus cannabinus* (kenaf—*malvaceae*) and *Carica papaya* (*papaya*—Caricaceae) was also reported. In the Mediterranean region the disease does occur in various crop species in Italy (Sicilia), Spain and Tunisia. In Asian countries, infection was proven in different crops in Bangladesh, India, Indonesia, Pakistan, Philippines, Sri Lanka, Taiwan and Thailand. Further information on geographical distribution of ToLCNDV is lacking, but from the observations made today, the virus clearly seems to further spread geographically as well as to other crops.

Disease symptoms in general comprise phenotypic appearance of yellow mosaic on leaves, leaf curling, vein swelling, and plant stunting. Cucurbits upon infection of young plants with ToLCNDV show stunted growth and decreased or suppressed fruit production. Also fruits showing skin roughness and longitudinal cracking have been reported. Thus, ToLCNDV causes economic losses in various important crop species and is a major threat. Infection of plants by ToLCNDV occurs persistently by transmission of the virus by the phloem sucking whitefly (*Bemisia tabaci*). (European and Mediterranean Plant Protection Organization, EPPO RS 2015/114, 2016/024, 2016/040, Entry date 2015-06).

In sponge gourd resistance to ToLCNDV has been shown to be controlled by a single dominant gene (Islam et al., 2010, Euphytica 174(1):83-89).

In tomato, transgenic plants resistant to ToLCNDV have been produced by silencing virus genes (Varma & Praveen, 2006, ISB News Report).

Assays for transmission of ToLCNDV by mechanically transferring the sap of an infected zucchini plant to non-infected plants from other cucurbit genera (*Cucumis, Cucurbita, Citrullus, Lagenaria*) have been developed. Five *Cucumis melo* subsp. *agrestis* accessions (subsp. *agrestis* var. *momordica*: Mom-KhaInd/Kharbuja, Mom-PI124Ind/PI124112, Mom-PI124Ind/PI414723 and subsp. *agrestis* wild types: Ag-WM9Ind/WM9, Ag-WM7Ind/WM7) resistant to ToLCNDV were identified (Lopez et al., 2015, Euphytica 204(3), 679-691). Confirmation of resistance of these accessions by using the natural whitefly infection system was not performed.

Saez et al. 2016, pages 214-216 (Proceedings of Cucurbitaceae 2016, the XIth EUCARPIA Meeting on Genetics and Breeding of Cucurbitaceae Jul. 24-28, 2016, Warsaw, Poland) describe that ToLCNDV resistance of the *C. melo* subsp. *agrestis* accession WM-7 segregated in an F2 population in a 3:1 ratio of tolerant: susceptible, suggesting a single dominant resistance gene being present in WM-7. As in Lopez et al. 2015, supra, mechanical inoculation was used, and not natural infection via whitefly vector. In a later publication (Saez et al., 14 Jul. 2017, Plant Cell Report, DOI 10.1007/s00299-017-2175-3), the resistance from WM-7 was mapped and found to be conferred by a dominant QTL on chromosome 11.

WO2017/114848 describe a ToLCNDV tolerance conferring QTL of a *C. melo* subsp. *agrestis* var. acidulous donor (referred to as H-MLCND-32) mapped to chromosome 11, which is recessive. A mix of two lines containing the QTL (RIL-69 and RIL-82) were deposited under accession number NCIMB 42506. According to Table 5, the QTL must lie in the sub-region between SEQ ID NO: 7 (Melon_sbg_33761_74) and SEQ ID NO: 16 (Melon_sbg_16835_17), because RIL-30 has the resistance phenotype, but lacks the donor SNP markers for SEQ ID NO: 1 (Melon_sbg_617_42) to 6 (Melon_sbg_60684_74). Three SNPs were found to have the most predictive value for the phenotype, namely Melon_sbg_33761_74 (SEQ ID NO: 7), Melon_sbg_2720_78 (SEQ ID NO: 8) and Melon_sbg_14207_58 (SEQ ID NO: 9) (see page 13, line 29-30 and FIG. 2). The donor is described to vary in symptom levels, e.g. of 7 plants, 4 had no symptoms, 2 had moderate yellowing symptoms and 1 was completely symptomatic (Table 1).

Various *Cucurbita* species (*C. pepo, C. moschata, C. maxima, C. fraternal, C. ficifolia*) have been screened for resistance to ToLCNDV by the mechanical sap transmission screening assay. Four *Curcubita moschata* accessions (PI 604506, PI 381814, Nigerian local, Kurokawa) were found to show low symptoms upon, mechanical infection with ToLCNDV. This result however could be reproduced upon whitefly infection only for two of the accession (PI 604506, PI 381814), demonstrating that resistance to ToLCNDV should be tested not only under artificial conditions but in addition by using the naturally occurring whitefly infection system (Saez et al., 2016, Annals of Applied Biology). Therefore, it is unclear if the accessions identified to be resistant to infection by ToLCNDV are resistant under natural growing conditions when the virus is transferred by whiteflies.

Attempts to control ToLCNDV infection of crop plants comprise vector (whitefly) control by insecticides applications and adaption of cultural practices, including use of virus free crop material (transplants), establishment of crop free periods, weed management (eliminating virus infected weeds) and destruction of infected plants in the field. However, because of the complex epidemiological factors associated with the disease, these attempts are not always effective (Saez et al., 2016, Annals of Applied Biology).

Therefore, there is a need to establish further measurements for reducing ToLCNDV infections, further spreading of the virus to other geographical areas and spreading to other crop species. Breeding of varieties resistant to ToLCNDV would be essential for managing the disease.

An object of the present invention is to provide measurements for the control of ToLCNDV infection in cultivated melon plants.

The present invention discloses cultivated melon plant cells and melon plants being resistant or even highly resistant to infections by ToLCNDV.

It is commonly known that ToLCNDV does infect various different plant species of the Cucurbitaceae species, including melon species. It is also well known that ToLCNDV is transmitted persistently from infected plants to non-infected plants by the plant sucking pest *Bemisia tabaci* (whitefly). Transfer of ToLCNDV from one crop species to different crop species or even from weed species to crop species has been demonstrated. Whiteflies may pick up ToLCNDV from outside the controlled area even from different species and transfer it to melon plants grown in the controlled area. Whitefly vector control, therefore, is of limited effectiveness for preventing ToLCNDV infection. ToLCNDV resistant melon plants have the advantage that they would withstand infection with ToLCNDV without major yield losses, even if plants around the area where the melon plants are grown are infected with ToLCNDV.

The inventors found a ToLCNDV resistant donor accession of *C. melo* subsp. *melo*, obtained from France but, according to the descriptor, originating from western India, and have mapped the resistance in a segregating population, using whitefly infection with a Spanish ToLCNDV strain for resistance phenotyping. Two Quantitative Trait Loci (QTLs) were identified, one on chromosome 11 (QTL11) and one on chromosome 12 (QTL12) and introgressed from the donor accession into an elite Piel de Sapo melon line and into an elite Galia melon line. Seeds of the Piel de Sapo line, comprising both QTL11 and QTL12 introgressions in homozygous form, were deposited by Nunhems B.V. under Accession number NCIMB42625 on Aug. 10, 2016 in accordance with the Budapest Treaty. In these seeds the donor genotype for the Single Nucleotide Polymorphism (SNP) markers (SNP_01 to SNP_07) provided herein is present. The donor itself is not uniform and has very long (elongated) fruits with a narrow fruit diameter and a low brix. It also has other negative characteristics, such as a very weak attachment of the peduncle at maturity, a very short shelf life of the fruits, etc., i.e. it is not an accession of agronomic value. By identifying and transferring QTL11 and/or QTL12 from the donor into cultivated melon, it is now possible to make cultivated melon varieties and cultivars of high agronomique value (with uniform characteristics and marketable fruits having high brix and good shelf life) with resistance against ToLCNDV and thus it is possible to cultivate those melon varieties in ToLCNDV infested areas without yield loss.

"Melon plant cells" or "melon plants" or "cultivated melon plants or cells" also designated as muskmelon plant cells or muskmelon plants in the art shall be understood in context with the present invention to be plant cells originating from the species *Cucumis melo* or to be plants belonging to the species *Cucumis melo*. *Cucumis melo*, can be classified into: *C. melo* var. *cantalupensis, C. melo* var. inodorous and *C. melo* var. *reticulatus. C. melo* var. *cantalupensis* are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo* var. inodorous (or winter melons) can be subdivided into different types, such as Honeydew melon, Piel de Sapo, Sugar melon, Japanese melon, etc. *C. melo* var. *reticulatus* is the true muskmelon, with reticulated skin (netted) and includes Galia melons, Sharlyn melons and the North American cantaloupe.

Cultivated melon and the wild relatives of melon is/are diploid and has/have 12 pairs of homologous chromosomes, numbered 1 to 12.

"Resistant" or "being resistant to" shall be understood in context of the present invention to mean a plant which is a host species of a particular pathogen and can therefore be infected by a given pathogen, but wherein the plant comprises a genetic element (e.g. an introgression fragment) resulting in reduction of pathogen growth and/or spreading in the plant after infection compared to the susceptible plant lacking the genetic element. In context of the present invention "resistant" or "being resistant to" in particular refers to plant cells or plants being resistant to ToLCNDV. Resistance is a relative term which can span a range of (different) reactions in the plant cell or plant, triggered by pathogen infection. The effect of those reactions by the plant cell or plant can be measured by various means. Typically the effect is measured by defining a symptom level appearing in the plant cell or plant. Typically average symptoms (average disease score) of several plants of a line (e.g. 10 or more) are compared to average symptoms (average disease score) of several plants of a control line or variety, preferably a susceptible control line or variety. Thus at least 10 or more individual plants of a line or variety are scored at one time point and the average disease score is calculated. Concerning the present invention, the following commonly known symptom levels (or disease score) are applied according to phenotypic observations taken after ToLCNDV infection:

1=Dead plant

2=Severe mosaic and curling, chlorosis and growth reduction. No recovery

3=Strong mosaic and curling, chlorosis and growth reduction. No recovery

4=Curling and mosaic, chlorosis, no or mild growth reduction. No recovery 5=Curling and mosaic, chlorosis, no growth reduction. Slight recovery of the upper plant zone 6=Mild curling, mosaic and chlorosis, no growth reduction. Recovery of the upper middle plant 7=Mild curling, mosaic and chlorosis, no growth reduction. Symptoms appear only in the lower plant zone 8=Faint mosaic 9=No symptoms For determining the symptom level (or disease score) preferably young plants are infected with ToLCNDV. Young plants are preferably plants having the age of the first true leaf being expanded, preferably approximately 12-15 days after sowing. Infection is preferably carried out via feeding of the vector (*Bemisia*) carrying the virus. For this purpose plants are germinated and grown under optimal or close to optimal conditions. The symptom level is preferably determined at least once at e.g. 30 days after infection (or later, e.g. 31, 32, 33, 34, 35 days after infection). Optionally symptom level is determined twice or even three times at different time-points following infection to confirm the result, e.g. a first scoring at approximately 15, 20 or 25 days after infection and a second scoring at approximately 30 days after infection (or later, e.g. 31, 32, 33, 34, 35 days after infection) with ToLCNDV. See also the Examples. The average disease score is calculated for each line or variety at each time point. In one aspect a plant line or variety is said to be "resistant" against ToLCNDV infection if it has an average disease score of 7.0 or higher, while the susceptible control line or variety, such as variety Gandalf or Vedantrais, has an average disease score of 4.0 or less, 3.0 or less or 2.0 or less, when grown under the same conditions and infected in the same way. In another aspect a plant line or variety is said to be "highly resistant" against ToLCNDV infection if it has an average disease score of 8.0 or higher, preferably if it has an average disease score of 9.0, while the susceptible control line or variety, such as variety Gandalf (or Gandalf F1, Nunhems) or Vedantrais, has an average disease score of 4.0 or less, 3.0 or less or 2.0 or less, when grown under the same conditions and infected in the same way.

It has been observed that introgressions of specific fragments located on chromosome 11 (comprising QTL11) and 12 (comprising QTL12) from the same wild melon plant donor into cultivated melon plants confers resistance to ToLCNDV infection in cultivated melon plants or cells derived therefrom. While the fragment on chromosome 11 needs to be present in homozygous form to confer resistance, it is sufficient that the fragment on chromosome 12 is present only in the heterozygous state for conferring ToLCNDV resistance, demonstrating that the fragment on chromosome 11 confers resistance in a recessive manner, while the fragment on chromosome 12 confers resistance to ToLCNDV infection in a partially dominant manner. Single Nucleotide Polymorphisms (SNPs) on chromosome 11 and 12 were identified which are closely linked to the fragment of chromosome 11 and 12 conferring ToLCNDV resistance. The SNP genotype of the resistant donor (i.e. the nucleotide of the introgression fragment) is present in homozygous form in the deposited seeds, i.e. the donor genotype is present in homozygous form for SNP_01 to SNP_04 (linked to QTL11) and also for SNP_05 to SNP_07 (linked to QTL12). The SNPs can, therefore, be used to test the presence of the introgression fragment comprising the QTL11 or QTL12 in a plant cell, plant tissue, plant part, and/or in marker assisted selection (MAS) to transfer the QTLs into other elite melon lines or varieties. The SNPs can also be used to select plants comprising smaller introgressions fragments than the fragments present in the deposited seeds, whereby the smaller sub-fragments retain the QTL. Alternatively the SNPs can be used to identify other donors which comprise QTL11 and/or QTL12 and to introgress these QTLs into cultivated melon.

The present invention, therefore, relates in one aspect to cultivated melon plant cells or melon plants (or plant parts) comprising an introgression fragment from chromosome 11 and/or 12 of a ToLCNDV resistant donor plant, wherein the introgression fragment comprises the sequence of the donor plant in-between SNP_01 and SNP_04 for the fragment on chromosome 11, preferably in-between SNP_02 and SNP_04 for the fragment on chromosome 11 or optionally in-between SNP_03 and SNP_04; or optionally in-between SNP_01 and SNP_03, or in-between SNP_02 and SNP_03, or in-between SNP_01 and SNP_02; and/or in-between SNP_05 and SNP_07 for the fragment on chromosome 12, optionally in-between SNP_05 and SNP_06, or in-between SNP_06 and SNP_07. The ToLCNDV resistance conferring QTL is present on the introgression fragment, as can be determined by a resistance assay as described herein.

In one aspect the present invention relates to cultivated melon plant cells or melon plants (or plant parts) comprising an introgression fragment from chromosome 11 and/or 12 of a ToLCNDV resistant donor plant, wherein the introgression fragment confers ToLCNDV resistance and the introgression fragment is detectable by (comprises) the SNP genotype of the donor plant for one or more (or all) of the following SNPs: SNP_01, SNP_02, SNP_03 and/or SNP_04, and optionally any SNP in-between SNP_01 and SNP_04, for the fragment on chromosome 11; and/or wherein the introgression fragment confers ToLCNDV resistance and the introgression fragment is detectable by (comprises) the SNP genotype of the donor plant for one or more (or all) of the following SNPs: SNP_05, SNP_06 and/or SNP_07, and optionally any SNP in-between SNP_05 and SNP_07, for the fragment on chromosome 12. The ToLCNDV resistance conferring QTL is present on the introgression fragment as can be determined by a resistance assay as described herein.

In one aspect the SNP genotype for SNP_01, SNP_02, SNP_03 and/or SNP_04 is the SNP genotype of the introgression donor of QTL11, i.e. an Adenine (A) at nucleotide 101 of SEQ ID NO: 1 (SNP_01), a Guanine (G) at nucleotide 101 of SEQ ID NO: 2 (SNP_02), a Thymine (T) at nucleotide 101 of SEQ ID NO: 3 (SNP_03), a Thymine (T) at nucleotide 101 of SEQ ID NO: 4 (SNP_04).

In one aspect the plant, plant part or plant cell comprises QTL11 and comprises the SNP donor genotype for at least SNP_03, as this SNP is most significantly associated with the ToLCNDV resistance QTL11. In a further aspect the plant, plant part or plant cell comprises the SNP donor genotype for at least SNP_03 and SNP_04, or for at least SNP_03 and SNP_02. Optionally, the plant, plant part or plant cell comprises QTL11 and comprises the SNP donor genotype for SNP_01, SNP_02 and SNP_03; or for SNP_02, SNP_03 and SNP_04. In one aspect the plant, plant part or plant cell comprises QTL11 comprises the SNP donor genotype for all four SNPs (SNP_01, SNP_02, SNP_03 and SNP_04).

In one aspect the SNP genotype for SNP_05, SNP_06 and/or SNP_07, is the SNP genotype of the introgression donor of QTL12, i.e. a C (Cytosine) at nucleotide 101 of SEQ ID NO: 5 (SNP_05) and/or a Guanine (G) at nucleotide 101 of SEQ ID NO: 6 (SNP_06), and optionally a Thymine (T) at nucleotide 101 of SEQ ID NO: 7 (SNP_07). In one aspect the plant, plant part or plant cell comprises QTL12 and comprises the SNP donor genotype for at least SNP_06, as this SNP is most significantly associated with the ToLCNDV resistance QTL12. In a further aspect the plant, plant part or plant cell comprises the SNP donor genotype for at least SNP_05 and SNP_06, or for at least SNP_06 and SNP_07. Optionally, the plant, plant part or plant cell comprises QTL12 and comprises the SNP donor genotype for SNP_05 and SNP_06 and optionally also for SNP_07.

When referring herein to the introgression fragment comprising the donor chromosome sequence or a donor sequence (and the QTL) "in-between" two SNPs (Single Nucleotide Polymorphisms), this encompasses in one aspect that one or both of the two SNPs themselves are also from the resistant donor, i.e. have the donor nucleotide. Thus, regarding the QTL on chromosome 11, SNP_01, SNP_02, SNP_03 and SNP_04 may all have the resistant donor genotype. Or only SNP_01 and SNP_02 may have the resistant donor genotype; or only SNP_02 and SNP_03 may have the resistant donor genotype; or only SNP_03 and SNP_04 may have the resistant donor genotype. Or only a single SNP, i.e. only SNP_01, or only SNP_02 or only SNP_03, or only SNP_04 has the resistant donor genotype. The SNPs that do not have the resistant donor genotype thus have another genotype, the recipient genotype. The recipient genotype for a SNP may be any of the other 3 nucleotides, i.e. for SNP_01 the recipient genotype may be Cytosine, Guanine or Thymine.

Thus, for example when stating that the introgression fragment is in-between SNP_05 and SNP_06 regarding the QTL on chromosome 12, SNP_05 and SNP_06 may both have the resistant donor genotype. Or only a single SNP, i.e. only SNP_05 or only SNP_06 may have the resistant donor genotype. Optionally also SNP_07 may have the resistant donor genotype.

The reason that not all of the SNPs provided herein need to have the resistant donor genotype is that the introgression fragment comprising the QTL from the donor may be smaller than the chromosome fragment introgressed e.g. in the deposited seeds, but the fragment still comprises the QTL11 or QTL12. Still, a plant can be recognized to contain the introgression fragment (comprising the QTL11 or 12) by the phenotype, and/or by transferring the fragment to a susceptible plant and thereby transferring the ToLCNDV resistance phenotype, or by sequencing the region between the SNP markers to identify the donor fragment, or other methods known to the skilled person, such as saturating the region with more SNP markers, allelism tests, identifying the causal gene, etc.

Thus, a combination of methods can be used to show that the QTL11 or QTL12 is present in a plant cell or plant, even if not for all of the linked SNPs the donor SNP genotype is present. QTL11 confers an average ToLCNDV resistance of at least 7.0 when transferred into a susceptible line or variety and is recessive. QTL12 confers an average ToLCNDV resistance score of at least 5.0 or 6.0 when transferred into a susceptible line or variety and is partially dominant. And when both QTLs are combined in a cultivated plant so that their phenotype is expressed, an average ToLCNDV resistance score of at least 8.0 or at least 9.0 is obtained.

When QTL12 is transferred into a melon plant which already has some level of ToLCNDV resistance, it increases the average resistance level by 1 or 2 scores, so e.g. if the recipient plant has an average resistance level of 7.0, introduction of QTL12 will increase the resistance level to at least 8.0 or 9.0.

Thus, in one aspect the SNP genotype of the melon plant comprising the introgression fragment on chromosome 11 is the resistant donor genotype, i.e. in one aspect at least one, optionally at least two, optionally all three, or optionally all four of the following four SNPs on chromosome 11 has the genotype of the resistant donor as indicated in the Table below. As the introgression fragment on chromosome 11 needs to be in homozygous form to confer the ToLCNDV resistance phenotype, the SNP genotype is indicated in homozygous form.

In another aspect the SNP genotype of the melon plant comprising the introgression fragment on chromosome 12 is the resistant donor genotype, i.e. in one aspect at least one, optionally at least two of the SNPs on chromosome 12, selected from SNP_05, SNP_06 and SNP_07, has/have the genotype of the resistant donor as indicated in the Table 1 below. Optionally all three SNPs have the resistant donor genotype as indicated in the Table 1 below. Although the introgression fragment on chromosome 12 does not need to be in homozygous form to confer the ToLCNDV resistance phenotype, homozygous form is preferred. Therefore the SNP genotype is indicated in homozygous form.

It is noted that SNP_01, SNP_02, SNP_03 and SNP_04 are physically located on chromosome 11 in that order, as are SNP_05, SNP_06 and SNP_07 on chromosome 12. An introgression fragment may therefore comprise the donor SNP genotype for all four SNP markers linked to QTL11 and/or for all three SNP markers linked to QTL12 (as in the seeds deposited herein), or a smaller fragment, whereby one or more of the SNP markers is not present. As described further below, even all or all but one donor SNP markers may be absent, while QTL11 or QTL12 is still present on the introgression fragment.

TABLE 1

| SNP (Single Nucleotide Polymorphism) | Resistant donor SNP genotype (in homozygous form) | QTL on Chromosome |
|---|---|---|
| SNP_01 refers to nucleotide 101 of SEQ ID NO: 1 (or of a sequence comprising at least 90%, or at least 95%, 96%, 97%, 98% or 99% sequence identity to SEQ ID NO: 1) | AA | 11 |
| SNP_02 refers to nucleotide 101 of SEQ ID NO: 2 (or of a sequence comprising at least 90%, or at least 95%, 96%, 97%, 98% or 99% sequence identity to SEQ ID NO: 2) | GG | 11 |
| SNP_03 refers nucleotide 101 of SEQ ID NO: 3 (or of a sequence comprising at least 90%, or at least 95%, 96%, 97%, 98% or 99% sequence identity to SEQ ID NO: 3) | TT | 11 |
| SNP_04 refers nucleotide 101 of SEQ ID NO: 4 (or of a sequence comprising at least 90%, or at least 95%, 96%, 97%, 98% or 99% sequence identity to SEQ ID NO: 4) | TT | 11 |

TABLE 1-continued

| SNP (Single Nucleotide Polymorphism) | Resistant donor SNP genotype (in homozygous form) | QTL on Chromosome |
|---|---|---|
| SNP_05 refers nucleotide 101 of SEQ ID NO: 5 (or of a sequence comprising at least 90%, or at least 95%, 96%, 97%, 98% or 99% sequence identity to SEQ ID NO: 5) | CC | 12 |
| SNP_06 refers nucleotide 101 of SEQ ID NO: 6 (or of a sequence comprising at least 90%, or at least 95%, 96%, 97%, 98% or 99% sequence identity to SEQ ID NO: 6) | GG | 12 |
| SNP_07 refers nucleotide 101 of SEQ ID NO: 7 (or of a sequence comprising at least 90%, or at least 95%, 96%, 97%, 98% or 99% sequence identity to SEQ ID NO: 7) | TT | 12 |

The nucleotide sequences (SEQ ID NO: 1 to SEQ ID NO: 7) comprising the SNPs provided herein are the nucleotide sequences of the resistant donor, i.e. they contain the donor SNP nucleotide. Therefore, in one aspect the present invention relates to cultivated melon plant cells or melon plants (or plant parts) comprising an introgression fragment from chromosome 11 and/or 12 of a ToLCNDV resistant donor plant, wherein the introgression fragment confers ToLCNDV resistance and the introgression fragment is detectable by (comprises) SEQ ID NO: 1 or an Adenine at nucleotide 101 of SEQ ID NO: 1 or an Adenine at the equivalent nucleotide of a sequence having substantial sequence identity to SEQ ID NO: 1 and/or by SEQ ID NO: 2 or a Guanine at nucleotide 101 of SEQ ID NO: 2 or a Guanine at the equivalent nucleotide of a sequence having substantial sequence identity to SEQ ID NO:2 and/or by SEQ ID NO: 3 or a Thymine at nucleotide 101 of SEQ ID NO: 3 or a Thymine at the equivalent nucleotide of a sequence having substantial sequence identity to SEQ ID NO: 3 and/or by SEQ ID NO: 4 or a Thymine at nucleotide 101 of SEQ ID NO: 4 or a Thymine at the equivalent nucleotide of a sequence having substantial sequence identity to SEQ ID NO: 4 for the fragment on chromosome 11; and/or wherein the introgression fragment confers ToLCNDV resistance and the introgression fragment is detectable by (comprises) SEQ ID NO: 5 or a Cytosine at nucleotide 101 of SEQ ID NO: 5 or a Cytosine at the equivalent nucleotide of a sequence having substantial sequence identity to SEQ ID NO:5 and/or by SEQ ID NO: 6 or a Guanine at nucleotide 101 of SEQ ID NO: 6 or a Guanine at the equivalent nucleotide of a sequence having substantial sequence identity to SEQ ID NO: 6 and/or by SEQ ID NO: 7 or a Thymine at nucleotide 101 of SEQ ID NO: 7 or a Thymine at the equivalent nucleotide of a sequence having substantial sequence identity to SEQ ID NO: 7 for the fragment on chromosome 12. The ToLCNDV resistance conferring QTL is present on the introgression fragment.

In one aspect only the QTL on chromosome 11 or only the QTL on chromosome 12 is introgressed into cultivated melon. The QTL on chromosome 11 has a better effect on ToLCNDV resistance (when in homozygous form) than the QTL on chromosome 12. The QTL on chromosome 11 confers an average ToLCNDV resistance score of at least 7.0 to the cultivated melon, compared to an average score of 4.0 or less, or 3.0 or less of a control line or variety lacking the QTL, such as a ToLCNDV susceptible variety.

The QTL on chromosome 12, on the other hand, also confers ToLCNDV resistance when it is in heterozygous form. The QTL on chromosome 12 confers an average ToLCNDV resistance score of at least 5.0 or at least 6.0 to the cultivated melon, compared to a score of 4.0 or less, or 3.0 or less of a control line or variety lacking the QTL, such as a ToLCNDV susceptible variety.

In another aspect both QTLs, the QTL on chromosome 11 and the QTL on chromosome 12, are introgressed into cultivated melon. In one aspect at least the QTL on chromosome 11 is in homozygous form. In another aspect, both QTLs are in homozygous form. The presence of both QTLs, with both QTLs in homozygous form, provides the highest average resistance score, of at least 8.0, preferably a score of 9.0 (no symptoms).

The donor has an average score of 9.0 (no symptoms). Off course other donors, which have an average score of 9.0 may also contain QTL11 and/or QTL12. The SNP markers provided herein can be used to screen such donors for the presence of QTL 11 and QTL12.

In another aspect, one or more, or even all, or all but one of the SNPs linked to the QTL may be from the recipient, e.g. the susceptible melon plant, while the region between the SNPs is from the resistant donor and confers ToLCNDV resistance, i.e. the resistance conferring donor fragment lies in-between the SNP markers. For example, a plant may comprise the introgression fragment comprising the sequence of the ToLCNDV resistant donor melon plant (carrying QTL11) in-between SNP_03 and SNP_04, this plant in one aspect comprises a Cytosine (C) at nucleotide 101 of SEQ ID NO: 3 and a Cytosine (C) at nucleotide 101 of SEQ ID NO: 4, i.e. the recipient nucleotides, not the donor. Thus, in one aspect only a region (the whole region or a part thereof) between these two SNPs is from the donor, while SNP_03 and SNP_04 are from the recipient, having a Cytosine (C) at nucleotide 101 of SEQ ID NO: 3 and a Cytosine (C) at nucleotide 101 of SEQ ID NO: 4. The same holds for other pairs of SNPs.

In one aspect, at least SNP_04 in the cultivated melon plant, plant part or plant cell of the invention is from the resistant donor and has the donor genotype, i.e. the introgression fragment comprises QTL11 and SEQ ID NO: 4.

In another aspect, at least SNP_06 in the cultivated melon plant, plant part or plant cell of the invention is from the resistant donor and has the donor genotype, i.e. the introgression fragment comprises QTL12 and SEQ ID NO: 6.

In a preferred embodiment of the invention the introgression fragment from chromosome 11 of the donor plant comprising the sequence of the donor plant (comprising QTL11) in-between SNP_01 and SNP_04, or in-between SNP_01 and SNP_03, or in-between SNP_01 and SNP_02, or between SNP_02 and SNP_04, or in-between SNP_02 and SNP_03, or in-between SNP_03 and SNP_04, or preferably in-between SNP_02 and SNP_04 confers resistance to ToLCNDV to the melon plant cells according to the invention or to the melon plants according to the invention.

In a preferred embodiment of the invention the introgression fragment from chromosome 12 of the donor plant comprising the sequence of the donor plant (comprising QTL12) in-between SNP_05 and SNP_07, or in between SNP_05 and SNP_06, or in-between SNP_06 and SNP_07 confers resistance to ToLCNDV to the melon plant cells according to the invention or to the melon plants according to the invention.

Preferably, the melon plant cell according to the invention originates from a cultivated melon plant or the melon plant according to the invention, is a cultivated melon plant.

"Donor plant cell" or "donor plant" in connection with the present invention shall mean a melon plant cell or melon plant being resistant to ToLCNDV, preferably having an average resistance score of at least 9.0. Likewise, the term DNA fragment or introgression fragment from the donor plant or cell shall mean a fragment of chromosome 11 or 12 of a melon plant resistant to ToLCNDV, whereby the fragment confers ToLCNDV resistance when transferred into a ToLCNDV susceptible melon plant. In one embodiment of the invention, the donor plant is a wild species or wild accession of melon. In one embodiment of the invention, DNA fragments or introgression fragments from donor plant cells or plants are the donor fragments obtained from, or obtainable from, or as present in, plants grown from seeds deposited under NCIMB 42625 or progeny obtained from plants grown from seeds deposited under NCIMB 42625 or plants obtained by crosses with plants grown from seeds deposited under NCIMB 42625. As mentioned, the deposited seeds are of cultivated melon (Piel de Sapo), into which QTL 11 and QTL12 has been introgressed from a donor plant which had an average disease score of 9.0.

Donor melon plants can be obtained from various sources. A person skilled in the art knows how to detect other sources of ToLCNDV resistant donor plants. For detecting such sources of ToLCNDV resistant donor plants, basically melon plants can be infected with ToLCNDV, either by mechanical means, as described in Lopez et al. (2015, Euphytica 204(3), 679-691) or by transmission of the virus by whiteflies. Preferably, infection occurs by whitefly infection in context with the present invention. Plants showing reduced symptom levels compared to susceptible controls can then be selected and used as source for genome fragments or sequences conferring ToLCNDV resistance. A preferred method on how to infect melon plants with ToLCNDV and methods for determining the symptom level of infected plants are given herein under "General Methods".

In context of the present invention the donor plants preferably have an average symptom level equal to or above 8.0 and most preferred equal to or above 9.0. In one aspect the donor plant comprises the same SNP genotype as shown in Table 3 for the donor for SNP_01, SNP_02, SNP_03 and SNP_04. In one aspect the donor plant comprises the same SNP genotype as shown in Table 3 for the donor for SNP_01, SNP_02, SNP_03 and SNP_04 and for SNP_05, SNP_06, and optionally also for SNP_07. Preferably the SNP donor genotype is homozygous.

"Recurrent plant cell" or "recurrent plant" or "recipient plant" in connection with the present invention shall be understood to be a melon plant cell or melon plant being sensitive (used herein synonymously with susceptible) or non-resistant to ToLCNDV infection. If a plant is sensitive or non-resistant to ToLCNDV can be determined by observation of the symptom levels after ToLCNDV infection. A recurrent plant preferably has an average symptom level equal to or below 4.0, equal to or below 3.0, more preferably equal to or below 2.0. Symptom levels and methods how to infect melon plants with ToLCNDV are described elsewhere herein and are applicable here accordingly. In a preferred embodiment of the invention, the recurrent melon plant cell according to the invention originates from a cultivated melon plant or the recurrent melon plant according to the invention, is a cultivated melon plant. Preferably it is an elite line, breeding line or variety.

"Introgression fragment" refers to a chromosome fragment, chromosome part or region which has been introduced into another plant of the same or related species by crossing or traditional breeding techniques. The introgression of the fragment from a donor plant into a recurrent plant introduces into the offspring of a cross between the donor and recurrent plant a phenotype, which was not present in the recurrent plant. Concerning the present invention, the phenotype transferred from the donor plant to the recurrent plant is resistance to ToLCNDV, especially an average disease score of 7.0 or more, 8.0 or more or 9.0 or more. For introgression of a fragment into a specific elite line or variety the first crossing step can e.g. be followed by one or more backcrossings with the intended elite line or variety. As understood herein, introgression can mean a first crossing of a ToLCNDV resistant donor plant with a ToLCNDV non-resistant recurrent plant and further back-crossing one or several times ToLCNDV resistant plants obtained from the crossing with plants of the recipient into which ToLCNDV resistance shall be introgressed. In such a case, the introgressed fragment is the result of breeding methods referred to by the verb "to introgress" (such as backcrossing) into a recipient variety or breeding line or elite line. Thus, introgression of ToLCNDV resistance into a recurrent plant is a technical process directed by man. In particular introgression herein refers to a man-made breeding process or method. One or more or all of the molecular markers provided herein can be used in that process. The resulting plant, i.e. the cultivated line or variety comprising one or two introgression fragments from a donor is also man-made and does not exist in nature.

The introgression fragment can be large, e.g. even half of a chromosome, but is preferably smaller, such as about 15 Mb (Megabases) or less, such as about 10 Mb or less, about 9 Mb or less, about 8 Mb or less, about 7 Mb or less, about 6 Mb or less, about 5 Mb or less, about 4 Mb or less, about 3.5 or 3 Mb or less, about 2 Mb or less, about 1 Mb (equals 1,000,000 base or less), or about 0.9 Mb (equals 900,000 base pairs) or less, such as 0.8 Mb, 0.7 Mb, 0.6 Mb, 0.5 Mb, 0.4 Mb, 0.3 Mb, or less.

The physical distance between SNP_01 and SNP_04 is about 1.16 Mb, and the physical distance between SNP_05 and SNP_06 is about 0.88 Mb and between SNP_05 and SNP_07 about 3.4 Mb. So in one aspect the introgression fragment comprises the elsewhere herein indicated physical region comprising one or more of the SNPs, or a sub-region thereof, which retains the QTL.

The introgression fragment can originate from e.g. a wild melon plant or wild melon accession or wild relatives of melon or landraces (donor). Wild melon plants or wild melon accessions or wild relatives of melon plants or landraces can be used to introgress fragments of the donor genome into the genome of cultivated melon, *Cucumis melo*, to generate elite lines and varieties with good agronomic characteristics. Such a cultivated melon plant thus has a "genome of cultivated *C. melo*", but comprises in its genome a fragment of the donor, e.g. an introgression fragment of a related *Cucumis* genome, such as *Cucumis melo* ssp. *agrestis, C. melo* ssp. *melo, C. melo* ssp. acidulous, *C. callosus,*

*C. trigonus, C. picrocarpus*, or another wild melon or wild relative of melon. It is understood that the term "introgression fragment" never includes a whole chromosome, but only a part of a chromosome. The chromosomes carrying the introgression therefore also comprise a part or parts of the recurrent (recipient) melon plant and in addition parts of the donor melon plant.

In one aspect the donor plant of the invention is not one of the five *Cucumis melo* subsp. *agrestis* accessions (subsp. *agrestis* var. *momordica*: Mom-KhaInd/Kharbuja, Mom-PI124Ind/PI124112, Mom-PI124Ind/PI414723 and subsp. *agrestis* wild types: Ag-WM9Ind/WM9, Ag-WM7Ind/WM7) resistant to ToLCNDV identified by Lopez et al., 2015, Euphytica 204(3), 679-691.

In another aspect the donor plant of the invention is not an accession belonging to the subspecies (abbreviated as 'ssp' or 'subsp.') *agrestis*, i.e. it is not a *Cucumis melo* ssp *agrestis* accession, especially in one aspect the donor is not a *Cucumis melo* ssp *agrestis* var. acidulous accession. In one aspect the resistance donor is a *Cucumis melo* ssp. *melo* accession.

The term "breeding" encompasses herein crossing, backcrossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 11 or 12 can be obtained, identified, produced and/or transferred.

In a preferred embodiment of the present invention, the introgression fragment originates form a wild *Cucumis* plant or a wild *Cucumis* accession or a landrace, most preferably the introgression fragment originates from a *Cucumis melo* ssp. *melo*, having one or more of the following characteristics: a low brix or a low percentage of TSS (total soluble solids, e.g. less than 6% Total Soluble Solids or less than 5.5% TSS), a very weak attachment of the peduncle at fruit maturity (on a scale of very weak, weak, medium, strong, very strong, see UPOV characteristic 39 in TG/104/5 Rev., UPOV Code: CUCUM_MEL, found on the website UPOV.int), a very short shelf life of the fruit (on a scale of very short, short, medium, long, very long; see UPOV characteristic 68 in TG/104/5 Rev., UPOV Code: CUCUM_MEL, found on the website UPOV.int).

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

"Uniformity" or "uniform" relates to the genetic and phenotypic characteristics of a plant line or variety. Inbred lines are genetically highly uniform as they are produced by several generations of inbreeding. Likewise, and the F1 hybrids which are produced from such inbred lines are highly uniform in their genotypic and phenotypic characteristics and performance.

"Chromosome 11 of a melon plant" is to be understood in context of the present invention as the scaffolds, fragments, regions, markers and nucleic acid sequences assigned by the ICuGI (International Cucurbit Genomics Initiative) to belong to chromosome 11 of the melon genome or preferably by melonomics.net assigned to chromosome 11. On melonomics.net one can BLAST sequences against the melon genome scaffolds under Old Melonomics (v3.5) or against the melon genome version CM3.5.1 or CM3.6.1 (New Melonomics v4.0).

"Orthologous chromosome 11" refers to the chromosome 11 of donor plants, parts of which can be introgressed into cultivated melon chromosome 11.

"Chromosome 12 of a melon plant" is to be understood in context of the present invention as the scaffolds, fragments, regions, markers and nucleic acid sequences assigned by the ICuGI (International Cucurbit Genomics Initiative) to belong to chromosome 12 of the melon genome or preferably by melonomics.net assigned to chromosome 12.

"Orthologous chromosome 12" refers to the chromosome 12 of donor plants, parts of which can be introgressed into cultivated melon chromosome 12.

"ICuGI" refers herein to the *Cucumis melo* data published by the International Cucurbit Genomics Initiative, which publishes genetic maps of e.g. *Cucumis melo* (http://www.icugi.org/cgi-bin/cmap/map set_info?species acc=CM), but which was renewed in May 2017 and can be found at cucurbitgenomics.org. Further information including additional markers and mapping information in addition to the ICuCI data is available from Diaz et al. (2015, Mol Breeding 35, 188) and the additional data included in the online version of the respective article.

Scaffold CM3.5 scaffold00052 of melonomics.net corresponds to chromosome 11 (under Old Melonomics v3.5). Scaffold CM3.5_scaffold00004 of melonomics.net corresponds to chromosome 12 (under Old Melonomics v3.5). If one BLASTs any of the sequences of SEQ ID NO: 1 to SEQ ID NO: 7 provided herein against the published sequence of the melon genome of the melonomics.net database (under Old Melonomics v3.5), the alignment with the scaffold will be shown. If one BLASTs any one of SEQ ID NO: 1 to SEQ ID NO: 7 provided herein against the CM3.6.1 genome or the CM3.5.1 genome (under New Melonomics v4.0), the chromosome and alignment with the chromosome part of the genome will be shown.

"Cultivated melon plant" refers to plants of *Cucumis melo* i.e. varieties, breeding lines or cultivars of the species *C. melo*, cultivated by humans and having good agronomic characteristics, especially producing edible and marketable fruits of good size and quality and uniformity; preferably such plants are not "wild melon plants", i.e. plants which generally have much poorer yields and poorer agronomic characteristics than cultivated plants and e.g. grow naturally in wild populations. "Wild melon plants" include for example ecotypes, PI (Plant Introduction) lines, landraces or wild accessions or wild relatives of a species.

A "SNP (=Single Nucleotide Polymorphism)" in context with the present invention is to be understood as a variation in a single nucleotide that occurs at a specific position in the genome. A SNP is the variation of the single nucleotide at the given position in a genome between two plants. If a wild melon plant having a ToLCNDV resistance (donor plant) shows in its corresponding sequence at a specific single position a nucleotide which is different from the corresponding nucleotide at the same position of a cultivated melon plant, the position defines a SNP between the wild melon and the cultivated melon. If the donor plant has one of the four possible nucleotides (A, C, T or G) at a specific position, a SNP occurs, when the cultivated plant has either of the remaining three possible nucleotides at the same corresponding sequence position. In a cultivated melon plant comprising an introgression fragment from a donor, it can therefore easily be determined if the single nucleotide of the SNP is from the donor or from the cultivated melon (recipient).

"SNP_01" which is alternatively designated "mME72223" is to be understood in context with the present invention to be a SNP at position 101 in SEQ ID NO: 1. SEQ ID NO:1 or a sequence substantially identical to SEQ ID NO:1 can be found on chromosome 11 in e.g. the ICuGI data set or on melonomics.net. The relative position of SNP_01 on the physical chromosome can be found in Table 2. Also the position on the genome version CM3.6.1 (New Melonomics v4.0) is shown. Preferably the nucleotide sequence comprising SNP_01 has a nucleotide sequence having at least 85% sequence identity with the nucleotide sequence shown under SEQ ID NO: 1, more preferably at least 90% identity with the nucleotide sequence shown under SEQ ID NO: 1, further more preferably at least 95% identity with the nucleotide sequence shown under SEQ ID NO: 1, even more preferred at least 97% identity with the nucleotide sequence shown under SEQ ID NO: 1, even further more preferred at least 98% identity with the nucleotide sequence shown under SEQ ID NO: 1, in particular preferred at least 99% identity with the nucleotide sequence shown under SEQ ID NO: 1 under the provision that in each case the nucleotide at position 101 in SEQ ID NO: 1 is different from the corresponding nucleotide at the same position of the recurrent plant. Such sequences having at least 85%, 90%, 95%, 97%, 98%, 99% or more sequence identity to SEQ ID NO: 1 are referred to as having substantial sequence identity to SEQ ID NO: 1.

The ToLCNDV resistant donor plant used in the invention has an 'A' (Adenine) at position 101 of SEQ ID NO: 1. In a preferred embodiment of the invention, SNP_01 is characterized in that the recurrent plant has an C, G or T at position 101 in SEQ ID NO: 1. In one aspect the recurrent plant has a G at position 101 in SEQ ID NO: 1. In one embodiment of the invention, SNP_01 is characterized in that the ToLCNDV resistant donor plant, or introgression fragment derived from the donor plant, has a 'A' at position 101 in SEQ ID NO: 1 and the recurrent plant has a G at position 101 in SEQ ID NO: 1, or a C at position 101 or a T at position 101 of SEQ ID NO: 1 (or at the equivalent position of a sequence comprising substantial sequence identity to SEQ ID NO: 1).

"SNP_02" which is alternatively designated "mME72233" is to be understood in context with the present invention to be a SNP at position 101 in SEQ ID NO: 2. SEQ ID NO:2 or a sequence substantially identical to SEQ ID NO:2 can be found on chromosome 11 e.g. in the ICuGI data set or on melonomics.net. The relative position of SNP_02 on the physical chromosome can be found in Table 2. Also the position on the genome version CM3.6.1 (New Melonomics v4.0) is shown. Preferably the nucleotide sequence comprising SNP_02 has a nucleotide sequence having at least 85% sequence identity with the nucleotide sequence shown under SEQ ID NO: 2, more preferably at least 90% identity with the nucleotide sequence shown under SEQ ID NO: 2, further more preferably at least 95% identity with the nucleotide sequence shown under SEQ ID NO: 2, even more preferred at least 97% identity with the nucleotide sequence shown under SEQ ID NO: 2, even further more preferred at least 98% identity with the nucleotide sequence shown under SEQ ID NO: 2, in particular preferred at least 99% identity with the nucleotide sequence shown under SEQ ID NO: 2 under the provision that in each case the nucleotide at position 101 in SEQ ID NO: 2 is different from the corresponding nucleotide at the same position of the recurrent plant. Such sequences having at least 85%, 90%, 95%, 97%, 98%, 99% or more sequence identity to SEQ ID NO: 2 are referred to as having substantial sequence identity to SEQ ID NO: 2.

The ToLCNDV resistant donor plant used in the invention has an 'G' (Guanine) at position 101 of SEQ ID NO: 2. In a preferred embodiment of the invention, SNP_02 is characterized in that the recurrent plant has a C, A or T at position 101 in SEQ ID NO: 2. In one aspect the recurrent plant has an 'A' at position 101 in SEQ ID NO: 2. In one embodiment of the invention, SNP_02 is characterized in that the ToLCNDV resistant donor plant, or introgression fragment derived from the donor plant, has a 'G' at position 101 in SEQ ID NO: 2 and the recurrent plant has an 'A' at position 101 in SEQ ID NO: 2, or a C at position 101 or a T at position 101 of SEQ ID NO: 2 (or at the equivalent position of a sequence comprising substantial sequence identity to SEQ ID NO: 2).

"SNP_03" which is alternatively designated "mME72238" is to be understood in context with the present invention to be a SNP at position 101 in SEQ ID NO: 3. SEQ ID NO:3 or a sequence substantially identical to SEQ ID NO:3 can be found on chromosome 11 e.g. in the ICuGI data set or on melonomics.net. The relative position of SNP_03 on the physical chromosome can be found in Table 2. Also the position on the genome version CM3.6.1 (New Melonomics v4.0) is shown. Preferably the nucleotide sequence comprising SNP_03 has a nucleotide sequence having at least 85% sequence identity with the nucleotide sequence shown under SEQ ID NO: 3, more preferably at least 90% identity with the nucleotide sequence shown under SEQ ID NO: 3, further more preferably at least 95% identity with the nucleotide sequence shown under SEQ ID NO: 3, even more preferred at least 97% identity with the nucleotide sequence shown under SEQ ID NO: 3, even further more preferred at least 98% identity with the nucleotide sequence shown under SEQ ID NO: 3, in particular preferred at least 99% identity with the nucleotide sequence shown under SEQ ID NO: 3 under the provision that in each case the nucleotide at position 101 in SEQ ID NO: 3 is different from the corresponding nucleotide at the same position of the recurrent plant. Such sequences having at least 85%, 90%, 95%, 97%, 98%, 99% or more sequence identity to SEQ ID NO: 3 are referred to as having substantial sequence identity to SEQ ID NO: 3.

The ToLCNDV resistant donor plant used in the invention has an 'T' (Thymine) at position 101 of SEQ ID NO: 3. In a preferred embodiment of the invention, SNP_03 is characterized in that the recurrent plant has an C, A or G at position 101 in SEQ ID NO: 3. In one aspect the recurrent plant has a C at position 101 in SEQ ID NO: 3. In one embodiment of the invention, SNP_03 is characterized in that the ToLCNDV resistant donor plant, or introgression fragment derived from the donor plant, has a 'T' at position 101 in SEQ ID NO: 3 and the recurrent plant has a C at position 101 in SEQ ID NO: 3, or a A at position 101 or a G at position 101 of SEQ ID NO: 3 (or at the equivalent position of a sequence comprising substantial sequence identity to SEQ ID NO: 3).

"SNP_04" which is alternatively designated "mME72245" is to be understood in context with the present invention to be a SNP at position 101 in SEQ ID NO: 4. SEQ ID NO:4 or a sequence substantially identical to SEQ ID NO:4 can be found on chromosome 11 e.g. in the ICuGI data set or on melonomics.net. The relative position of SNP_04 on the physical chromosome can be found in Table 2. Also the position on the genome version CM3.6.1 (New Melonomics v4.0) is shown. Preferably the nucleotide sequence comprising SNP_04 has a nucleotide sequence having at least 85% sequence identity with the nucleotide sequence shown under SEQ ID NO: 4, more preferably at least 90% identity with the nucleotide sequence shown under SEQ ID NO: 4, further more preferably at least 95% identity with the nucleotide sequence shown under SEQ ID NO: 4, even more preferred at least 97% identity with the nucleotide sequence shown under SEQ ID NO: 4, even further more preferred at least 98% identity with the nucleotide sequence shown under SEQ ID NO: 4, in particular preferred at least 99% identity with the nucleotide sequence shown under SEQ ID NO: 4 under the provision that in each case the nucleotide at position 101 in SEQ ID NO: 4 is different from the corresponding nucleotide at the same position of the recurrent plant. Such sequences having at least 85%, 90%, 95%, 97%, 98%, 99% or more sequence identity to SEQ ID NO: 4 are referred to as having substantial sequence identity to SEQ ID NO: 4.

The ToLCNDV resistant donor plant used in the invention has an 'T' (Thymine) at position 101 of SEQ ID NO: 4. In a preferred embodiment of the invention, SNP_04 is characterized in that the recurrent plant has an C, A or G at position 101 in SEQ ID NO: 4. In one aspect the recurrent plant has a C at position 101 in SEQ ID NO: 4. In one embodiment of the invention, SNP_04 is characterized in that the ToLCNDV resistant donor plant, or introgression fragment derived from the donor plant, has a 'T' at position 101 in SEQ ID NO: 4 and the recurrent plant has a C at position 101 in SEQ ID NO: 4, or a A at position 101 or a G at position 101 of SEQ ID NO: 4 (or at the equivalent position of a sequence comprising substantial sequence identity to SEQ ID NO: 4).

"SNP_05" which is alternatively designated "mME72255" is to be understood in context with the present invention to be a SNP at position 101 in SEQ ID NO: 5. SEQ ID NO:5 or a sequence substantially identical to SEQ ID NO:5 can be found on chromosome 12 e.g. in the ICuGI data set or on melonomics.net. The relative position of SNP_05 on the physical chromosome can be found in Table 2. Also the position on the genome version CM3.6.1 (New Melonomics v4.0) is shown. Preferably the nucleotide sequence comprising SNP_05 has a nucleotide sequence having at least 85% sequence identity with the nucleotide sequence shown under SEQ ID NO: 5, more preferably at least 90% identity with the nucleotide sequence shown under SEQ ID NO: 5, further more preferably at least 95% identity with the nucleotide sequence shown under SEQ ID NO: 5, even more preferred at least 97% identity with the nucleotide sequence shown under SEQ ID NO: 5, even further more preferred at least 98% identity with the nucleotide sequence shown under SEQ ID NO: 5, in particular preferred at least 99% identity with the nucleotide sequence shown under SEQ ID NO: 5 under the provision that in each case the nucleotide at position 101 in SEQ ID NO: 5 is different from the corresponding nucleotide at the same position of the recurrent plant. Such sequences having at least 85%, 90%, 95%, 97%, 98%, 99% or more sequence identity to SEQ ID NO: 5 are referred to as having substantial sequence identity to SEQ ID NO: 5.

The ToLCNDV resistant donor plant used in the invention has an 'C' (Cytosine) at position 101 of SEQ ID NO: 5. In a preferred embodiment of the invention, SNP_05 is characterized in that the recurrent plant has an G, A or T at position 101 in SEQ ID NO: 5. In one aspect the recurrent plant has a T at position 101 in SEQ ID NO: 5. In one embodiment of the invention, SNP_05 is characterized in that the ToLCNDV resistant donor plant, or introgression fragment derived from the donor plant, has a 'C' at position 101 in SEQ ID NO: 5 and the recurrent plant has a Tat position 101 in SEQ ID NO: 5, or a G at position 101 or an A at position 101 of SEQ ID NO: 5 (or at the equivalent position of a sequence comprising substantial sequence identity to SEQ ID NO: 5).

"SNP_06" which is alternatively designated "mME72261" is to be understood in context with the present invention to be a SNP at position 101 in SEQ ID NO: 6. SEQ ID NO:6 or a sequence substantially identical to SEQ ID NO:6 can be found on chromosome 12 e.g. in the ICuGI data set or on melonomics.net. The relative position of SNP_06 on the physical chromosome can be found in Table 2. Also the position on the genome version CM3.6.1 (New Melonomics v4.0) is shown. Preferably the nucleotide sequence comprising SNP_06 has a nucleotide sequence having at least 85% sequence identity with the nucleotide sequence shown under SEQ ID NO: 6, more preferably at least 90% identity with the nucleotide sequence shown under SEQ ID NO: 6, further more preferably at least 95% identity with the nucleotide sequence shown under SEQ ID NO: 6, even more preferred at least 97% identity with the nucleotide sequence shown under SEQ ID NO: 6, even further more preferred at least 98% identity with the nucleotide sequence shown under SEQ ID NO: 6, in particular preferred at least 99% identity with the nucleotide sequence shown under SEQ ID NO: 6 under the provision that in each case the nucleotide at position 101 in SEQ ID NO: 6 is different from the corresponding nucleotide at the same position of the recurrent plant. Such sequences having at least 85%, 90%, 95%, 97%, 98%, 99% or more sequence identity to SEQ ID NO: 6 are referred to as having substantial sequence identity to SEQ ID NO: 6.

The ToLCNDV resistant donor plant used in the invention has an 'G' (Guanine) at position 101 of SEQ ID NO: 6. In a preferred embodiment of the invention, SNP_06 is characterized in that the recurrent plant has an C, A or T at position 101 in SEQ ID NO: 6. In one aspect the recurrent plant has a A at position 101 in SEQ ID NO: 6. In one embodiment of the invention, SNP_06 is characterized in that the ToLCNDV resistant donor plant, or introgression fragment derived from the donor plant, has a 'G' at position 101 in SEQ ID NO: 6 and the recurrent plant has an A at position 101 in SEQ ID NO: 6, or a C at position 101 or a T at position 101 of SEQ ID NO: 6 (or at the equivalent position of a sequence comprising substantial sequence identity to SEQ ID NO: 6).

"SNP_07" which is alternatively designated "mME72279" is to be understood in context with the present invention to be a SNP at position 101 in SEQ ID NO: 7. SEQ ID NO:7 or a sequence substantially identical to SEQ ID NO:7 can be found on chromosome 12 e.g. in the ICuGI data set or on melonomics.net. The relative position of SNP_07 on the physical chromosome can be found in Table 2. Also the position on the genome version CM3.6.1 (New Melonomics v4.0) is shown. Preferably the nucleotide sequence comprising SNP_07 has a nucleotide sequence having at least 85% sequence identity with the nucleotide sequence shown under SEQ ID NO: 7, more preferably at least 90% identity with the nucleotide sequence shown under SEQ ID NO: 7, further more preferably at least 95% identity with the nucleotide sequence shown under SEQ ID NO: 7, even more preferred at least 97% identity with the nucleotide sequence shown under SEQ ID NO: 7, even further more preferred at least 98% identity with the nucleotide sequence shown under SEQ ID NO: 7, in particular preferred at least 99% identity with the nucleotide sequence shown under SEQ ID NO: 7 under the provision that in each case the nucleotide at position 101 in SEQ ID NO: 7 is different from the corresponding nucleotide at the same position of the recurrent plant. Such sequences having at least 85%, 90%, 95%, 97%, 98%, 99% or more sequence identity to SEQ ID NO: 7 are referred to as having substantial sequence identity to SEQ ID NO: 7.

The ToLCNDV resistant donor plant used in the invention has an 'T' (Thymine) at position 101 of SEQ ID NO: 7. In a preferred embodiment of the invention, SNP_07 is characterized in that the recurrent plant has an C, A or G at position 101 in SEQ ID NO: 7. In one aspect the recurrent plant has a C at position 101 in SEQ ID NO: 7. In one embodiment of the invention, SNP_07 is characterized in that the ToLCNDV resistant donor plant, or introgression fragment derived from the donor plant, has a 'T' at position 101 in SEQ ID NO: 7 and the recurrent plant has a C at position 101 in SEQ ID NO: 7, or a G at position 101 or a A at position 101 of SEQ ID NO: 7 (or at the equivalent position of a sequence comprising substantial sequence identity to SEQ ID NO: 7).

TABLE 2

| Chromosome | Marker name | Scaffold (world wide web at melonomics.net Old Melonomics v3.5) | SNP nucleotide position on scaffold00052 or scaffold0004 | Physical position on the chromosome 11 or 12 according to Diaz et al. 2015* e.g. FIG. 1 | SNP nucleotide position on melon genome version CM3.6.1 (New Melonomics v4.0) on chromosome 12 or chromosome 12, respectively |
|---|---|---|---|---|---|
| 11 | CMPSNP475 | Scaffold00052 | 1308124 | 30277435 | |
| 11 | SNP_01 (mME72223) | Scaffold00052 | 1256506 | | 33240885 |
| 11 | SNP_02 (mME72233) | Scaffold00052 | 777406 | | 32761709 |
| 11 | SNP_03 (mME72238) | Scaffold00052 | 513312 | | 32497404 |
| 11 | SNP_04 (mME72245) | Scaffold00052 | 90616 | | 32074519 |
| 11 | ECM192 | Scaffold00052 | 32422 | 29001733 | |
| 12 | CMPSNP2002 | Scaffold00004 | 255636 | 12534642 | |
| 12 | SNP_05 (mME72255) | Scaffold00004 | 3413496 | | 9379373 |
| 12 | SNP_06 (mME72261) | Scaffold00004 | 4297467 | | 8494993 |
| 12 | SNP_07 (mME72279) | Scaffold00004 | 6896770 | | 5895390 |
| 12 | CMPSNP310 | Scaffold00004 | 7646165 | 5144113 | |

*SNP nucleotide position based on position in Diaz et al. 2015, Mol Breeding 35:188, p 1-7.

As can be seen, SNP_01, SNP_02, SNP_03 and SNP_04 lie in between CMPSNP_475 (at 30.27 Mb) and ECM192 (at 29.0 Mb) on the physical chromosome 11, i.e. at the lower half of chromosome 11. On the genome CM3.6.1 SNP_01, SNP_02, SNP_03 and SNP_04 lie in the region starting at 32.07 Mb and ending at 33.24 Mb of chromosome 11.

SNP_05, SNP_06 and SNP_07 lie in between CMPSNP_2002 (at 12.5 Mb) and CMPSNP_310 (at 5.1 Mb) on the physical chromosome 12, i.e. on the upper half of chromosome 12. On the genome CM3.6.1 SNP_05, SNP_06 and SNP_07 lie in the region starting at 5.89 Mb and ending at 9.37 Mb of chromosome 12.

The molecular markers described herein may be detected according to standard methods. For example SNP markers can be detected using a KASP-assay (see \Vww.kpbioscience.co.uk) or other assays. A KASP-assay has been developed for SNPs described herein. Respective details are disclosed in the Example section. Sequences used in the respective KASP-assays are given in the Sequence Listing. For developing KASP-assays for the SNPs two allele specific forward primers and one allele specific reverse primer were designed according to common general knowledge (see e.g. Allen et al. 2011, Plant Biotechnology J. 9, 1 0 86-1 099, especially p097-098 for KASP assay method).

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity defined further below). These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff &

Henikoff, 1 992, PNAS 89, 1 09 1 5-1 09 1 9). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits are preferably retrieved and aligned pairwise to compare sequence identity. Two proteins or two protein domains, or two nucleic acid sequences have "substantial sequence identity" if the percentage sequence identity is at least 85%, 90%, 95%, 98% or 99% (as determined by Emboss "needle" using default parameters, i.e. gap creation penalty=10, gap extension penalty=0.5, using scoring matrix DNAFULL for nucleic acids an Blosum62 for proteins). When reference is made to a nucleic acid sequence (e.g. DNA or genomic DNA) having "substantial sequence identity to" a reference sequence or having a sequence identity of at least 80%, e.g. at least 85%, 90%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridization conditions. In another embodiment, the nucleic acid sequence comprises one or more mutations compared to the given nucleotide sequence but still can be identified using stringent hybridisation conditions.

Cultivated melon plants comprising a ToLCNDV resistance conferring fragment introgressed from the donor on chromosome 11 and/or 12 show reduced symptoms when infected with ToLCNDV, while susceptible controls (lacking the introgression fragments on chromosome 11 and 12) show the expected severe symptoms in the same conditions.

In a preferred embodiment of the invention, plants according to the invention, or plant cells according to the invention, are characterized in that they upon infection with ToLCNDV show an average symptom level (or average disease score) of at least 7.0, more preferably at least 8.0 or 9.0. As mentioned previously, QTL11 confers high levels of resistance when the QTL is in homozygous form. A ToLCNDV susceptible plant into which the introgression fragment comprising QTL11 is introduced by e.g. backcrossing and which is selfed to generate a homozygous introgression fragment (comprising the donor genotype for one or more or all of SNP_01, SNP_02, SNP_03 and SNP_04 in homozygous form) will result in a plant which is highly resistant to ToLCNDV infection, having an average disease score of at least 7.0, preferably at least 8.0 or preferably at least 9.0. QTL12 confers a lower level of resistance than QTL11, but in a partially dominant manner. A TolCNDV susceptible plant into which the introgression fragment comprising QTL12 is introduced by e.g. backcrossing and optionally selfing to generate a homozygous introgression fragment (comprising the donor genotype for one or more or all of SNP_05, SNP_6 and SNP_07 in heterozygous or homozygous form), will result in a plant having a higher level of resistance, with an average disease score of at least 5.0, preferably at least 6.0.

Symptom levels following infection with ToLCNDV are assessed on a scale between 1 and 9, wherein 1 is defined to be the level with the most severe symptoms and 9 is defined as the highest resistance level, have been described herein above and are applicable here accordingly. A preferred test for determining the symptom levels is given below under "General Methods".

Resistance to ToLCNDV conferred by the introgression fragment on chromosome 11 is expressed in a recessive manner and, thus, can be observed only when both chromosomes 11 comprise the introgression fragment comprising QTL11 and the donor SNP genotype of one or more or all of the SNP markers provided herein (SNP_01, SNP_02, SNP_03 and SNP_04) and/or the introgression fragment comprising the sequence of the donor plant in-between the SNP markers of chromosome 11 disclosed herein.

Resistance to ToLCNDV conferred by the introgression fragment on chromosome 12 is expressed in a dominant manner and, thus, can be observed when one of the chromosomes 12 comprises the introgression fragment comprising QTL12 and the donor SNP genotype of one or more or all of the SNP markers provided herein (SNP_05, SNP_06 and SNP_07) and/or the introgression fragment comprising the sequence of the donor plant in-between the SNP markers of chromosome 12 disclosed herein.

A plant comprising both QTL11 in homozygous form and QTL12 in heterozygous or in homozygous form will have an average ToLCNDV disease score of at least 8.0, preferably at least 9.0, i.e. be highly resistant. Such a plant has the advantage that the resistance is based on two different QTLs, meaning that resistance breakdown is unlikely to occur.

Other specific embodiments of the present invention therefore relate to cultivated melon plants, plant parts and plant cell according to the invention wherein the introgression fragment from chromosome 11 of a ToLCNDV resistant donor plant comprising the sequence of the donor plant in-between SNP_01 and SNP_04, or in-between SNP_01 and SNP_03, or in-between SNP_01 and SNP_02, or in-between SNP_02 and SNP_04, or between SNP_02 and SNP_03, or in-between SNP_03 and SNP_04 is present in homozygous state. The introgression fragment comprises QTL11, and therefore confers high ToLCNDV resistance to the plant.

In another aspect the present invention relates to cultivated melon plants, plant parts and plant cell according to the invention wherein the introgression fragment from chromosome 12 of a ToLCNDV resistant donor plant comprising the sequence of the donor plant in-between SNP_05 and SNP_06, or in-between SNP_06 and SNP_07, or in-between SNP_05 and SNP_07 is present in heterozygous or homozygous state. The introgression fragment comprises QTL12, and therefore confers ToLCNDV resistance to the plant.

In a further aspect, a cultivated melon plant, plant part or plant cell is provided which comprises both QTL11 (in homozygous form) and QTL12 (in heterozygous or in homozygous form) in its genome, i.e. it comprises two introgression fragments as described above and elsewhere herein. Such a melon plant can for example be generated by crossing a plant comprising QTL11 with a plant comprising QTL12 and selecting progeny which comprise both introgression fragments and both QTLs. Also the seed deposit provided herein comprises both QTLs in homozygous form (with the resistant donor genotype being present in homozygous form for SNP_01, SNP_02, SNP_03, SNP_04, SNP_05, SNP_06 and SNP_07) can be used to transfer both QTLs into any other cultivated melon line or variety by crossing the plant with another melon plant and optionally by selecting progeny plants comprising the resistant donor genotype for at least one SNP marker selected from SNP_01, SNP_02, SNP_03 and SNP_04 and at least one SNP marker selected from SNP_05, SNP_06 and SNP_07, preferably at least one SNP marker selected from SNP_05 and SNP_06. Optionally progeny can be tested for ToLCNDV resistance as described. Preferably, but not necessarily, QTL11 and QTL12 are both from the same donor plant.

Table 3 illustrates the SNP genotype of melon plants or melon plant cells comprising the donor SNPs in homozygous form or heterozygous form, as well as the recurrent parent SNP genotype, lacking the introgression fragment.

| SNP and nucleotide position (nt) in the sequence | SNP genotype in melon plant comprising the donor fragment in homozygous form | SNP genotype in melon plant comprising the donor fragment in heterozygous form | SNP genotype of the recurrent parent, lacking the introgression fragment |
|---|---|---|---|
| SNP_01 (nt 101 of SEQ ID NO 1) | AA | AG | GG |
| SNP_02 (nt 101 of SEQ ID NO 2) | GG | AG | AA |
| SNP_03 (nt 101 of SEQ ID NO 3) | TT | TC | CC |
| SNP_04 (nt 101 of SEQ ID NO 4) | TT | TC | CC |
| SNP_05 (nt 101 of SEQ ID NO 5) | CC | TC | TT |
| SNP_06 (nt 101 of SEQ ID NO 6) | GG | AG | AA |
| SNP_07 (nt 101 of SEQ ID NO 7) | TT | TC | CC |

In one aspect the cultivated melon plants or cells of these plants comprise an introgression fragment from a donor on chromosome 11, which introgression fragment confers the ToLCNDV resistance, whereby the introgression fragment lies in-between SNP_01 and SNP_04 and whereby the introgression fragment comprises a Thymine (T) at nucleotide 101 of SEQ ID NO: 3 or at the equivalent nucleotide of a sequence comprising substantial sequence identity to SEQ ID NO: 3. In a further aspect the introgression fragment further comprises a Thymine (T) at nucleotide 101 of SEQ ID NO: 4 or at the equivalent nucleotide of a sequence comprising substantial sequence identity to SEQ ID NO: 4 and/or the introgression fragment further comprises a Guanine (G) at nucleotide 101 of SEQ ID NO: 2 or at the equivalent nucleotide of a sequence comprising substantial sequence identity to SEQ ID NO:2. Optionally the introgression fragment further comprises the resistant donor nucleotide of SNP_01.

In one aspect the cultivated melon plants or cells of these plants comprise an introgression fragment from a donor on chromosome 11, which introgression fragment confers the ToLCNDV resistance, whereby the introgression fragment lies in-between SNP_01 and SNP_04 and whereby the introgression fragment comprises a Thymine (T) at nucleotide 101 of SEQ ID NO: 3 or at the equivalent nucleotide of a sequence comprising substantial sequence identity to SEQ ID NO: 3 and the introgression fragment optionally further comprises the resistant donor nucleotide of SNP_02 and/or SNP_01. Optionally the introgression fragment further comprises the donor SNP genotype for SNP_04.

In one aspect the cultivated melon plants or cells of these plants comprise an introgression fragment from a donor on chromosome 11, which introgression fragment confers the ToLCNDV resistance, whereby the introgression fragment comprises the donor genomic sequence between at least SNP_02 and SNP_03, optionally including the donor SNP nucleotide for one or both of these SNP markers. So optionally the introgression fragment comprises SEQ ID NO: 2 and SEQ ID NO: 3 and the nucleotide sequence in-between SEQ ID NO: 2 and SEQ ID NO: 3 is also from the resistant donor. Thus, the introgression fragment comprises the entire region from SEQ ID NO: 2 to SEQ ID NO: 3.

In one aspect the cultivated melon plants or cells of these plants comprise an introgression fragment from a donor on chromosome 11, which introgression fragment confers the ToLCNDV resistance, whereby the introgression fragment comprises the donor genomic sequence in-between at least SNP_04 and SNP_03, optionally including the donor SNP nucleotide for one or both of these SNP markers. So optionally the introgression fragment comprises SEQ ID NO: 4 and SEQ ID NO: 3 and the nucleotide sequence in-between SEQ ID NO: 4 and SEQ ID NO: 3 is also from the resistant donor. Thus, the introgression fragment comprises the entire chromosome region from SEQ ID NO: 4 to SEQ ID NO: 3.

In another aspect the cultivated melon plants or cells of these plants comprise an introgression fragment from a donor on chromosome 11, which introgression fragment confers the ToLCNDV resistance, whereby the introgression fragment comprises the donor genomic sequence in-between at least SNP_04 and SNP_02, optionally including the donor SNP nucleotide for one or both of these SNP markers. So optionally the introgression fragment comprises SEQ ID NO: 4 and SEQ ID NO: 2 and the nucleotide sequence in-between SEQ ID NO: 4 and SEQ ID NO: 2 is also from the resistant donor. Thus, in this aspect, the entire chromosome region from SEQ ID NO: 2 to SEQ ID NO: 4 is from the donor and comprises SEQ ID NO: 2, 3 and 4.

In another aspect the cultivated melon plants or cells of these plants comprise an introgression fragment from a donor on chromosome 11, which introgression fragment confers the ToLCNDV resistance, whereby the introgression fragment comprises the donor genomic sequence in-between at least SNP_01 and SNP_03, optionally including the donor SNP nucleotide for one or both of these SNP markers. So optionally the introgression fragment comprises SEQ ID NO: 1 and SEQ ID NO: 3 and the nucleotide sequence in-between SEQ ID NO: 1 and SEQ ID NO: 3 is also from the resistant donor. Thus, in this aspect, the entire chromosome region from SEQ ID NO: 1 to SEQ ID NO: 3 is from the donor and comprises SEQ ID NO: 1, 2 and 3.

In another aspect the cultivated melon plants or cells of these plants comprise an introgression fragment from a donor on chromosome 11, which introgression fragment confers the ToLCNDV resistance, whereby the introgression fragment comprises the donor genomic sequence in-between at least SNP_01 and SNP_04, optionally including the donor SNP nucleotide for one or both of these SNP markers. So optionally the introgression fragment comprises SEQ ID NO: 1 and SEQ ID NO: 4 and the nucleotide sequence in-between SEQ ID NO: 1 and SEQ ID NO: 4 is also from the resistant donor. Thus, in this aspect, the entire chromosome region from SEQ ID NO: 1 to SEQ ID NO: 4 is from the donor and comprises SEQ ID NO: 1, 2, 3 and 4. The introgression fragment present in the deposited seeds comprises SEQ ID NO: 1, 2, 3 and 4. However, as SNP_03 is most closely linked to the resistance phenotype, the introgression fragment can be reduced in size, while still retaining the QTL. Thus, for example, SEQ ID NO: 1, or SEQ ID NO: 1 and 2, may be removed through recombination within the introgression fragment and replaced by cultivated melon sequences. Or SEQ ID NO: 4 may be removed through recombination within the introgression fragment and replaced by cultivated melon sequences. Or e.g. SEQ ID NO: 1 and SEQ ID NO: 4 may be removed through recombination on both sides of the introgression fragment. Likewise e.g. SEQ ID NO: 1 and SEQ ID NO: 2 on one side and SEQ ID NO: 4 on the other side of the fragment may be removed through recombination.

In another aspect the cultivated melon plants or cells of these plants comprise an introgression fragment from a donor on chromosome 12, which introgression fragment confers the ToLCNDV resistance, whereby the introgression fragment comprises a Guanine (G) at nucleotide 101 of SEQ ID NO: 6 or at the equivalent nucleotide of a sequence comprising substantial sequence identity to SEQ ID NO: 6. In a further aspect the introgression fragment further comprises a Cytosine (C) at nucleotide 101 of SEQ ID NO: 5 or at the equivalent nucleotide of a sequence comprising substantial sequence identity to SEQ ID NO: 5 and/or the introgression fragment further comprises a Thymine (T) at nucleotide 101 of SEQ ID NO: 7 or at the equivalent nucleotide of a sequence comprising substantial sequence identity to SEQ ID NO: 7.

In one aspect the cultivated melon plants or cells of these plants comprise an introgression fragment from a donor on chromosome 12, which introgression fragment confers the ToLCNDV resistance, whereby the introgression fragment comprises the donor genomic sequence between at least SNP_06 and SNP_05, optionally including the donor SNP nucleotide for one or both of these SNP markers. So optionally the introgression fragment comprises SEQ ID NO: 6 and SEQ ID NO: 5 and the nucleotide sequence in between SEQ ID NO: 6 and SEQ ID NO: 5 is also from the resistant donor. Thus, the introgression fragment comprises the entire chromosome region from SEQ ID NO: 6 to SEQ ID NO: 5.

In one aspect the cultivated melon plants or cells of these plants comprise an introgression fragment from a donor on chromosome 12, which introgression fragment confers the ToLCNDV resistance, whereby the introgression fragment comprises the donor genomic sequence between at least SNP_06 and SNP_07, optionally including the donor SNP nucleotide for one or both of these SNP markers. So optionally the introgression fragment comprises SEQ ID NO: 6 and SEQ ID NO: 7 and the nucleotide sequence in between SEQ ID NO: 6 and SEQ ID NO: 7 is also from the resistant donor. Thus, the introgression fragment comprises the entire chromosome region from SEQ ID NO: 6 to SEQ ID NO: 7.

In yet one aspect the cultivated melon plants or cells of these plants comprise an introgression fragment from a donor on chromosome 12, which introgression fragment confers the ToLCNDV resistance, whereby the introgression fragment comprises the donor genomic sequence between at least SNP_05 and SNP_07, optionally including the donor SNP nucleotide for one or both of these SNP markers. So optionally the introgression fragment comprises SEQ ID NO: 5 and SEQ ID NO: 7 and the nucleotide sequence in between SEQ ID NO: 5 and SEQ ID NO: 7 is also from the resistant donor. Thus, the introgression fragment comprises the entire chromosome region from SEQ ID NO: 5 to SEQ ID NO: 7. The introgression fragment present in the deposited seeds comprises SEQ ID NO: 5, 6 and 7. However, as SNP_06 is most closely linked to the resistance phenotype, the introgression fragment can be reduced in size, while still retaining the QTL. Thus, for example SEQ ID NO: 5 and/or SEQ ID NO: 7 may be removed through recombination within the introgression fragment and replaced by cultivated melon sequences.

As mentioned before, plants, plant parts and plant cells comprising both a introgression fragment on chromosome 11 and an introgression fragment on chromosome 12 are encompassed herein.

Plants comprising plant cells according to the invention are another embodiment of the invention.

The melon plant according to the invention may be an inbred line, an open pollinated variety (OP) or an F1 hybrid variety.

In one aspect the F1 hybrid comprises the introgression fragment on chromosome 11 and/or 12 in heterozygous form, i.e. produced by crossing two inbred parent lines, one of which possesses the introgression fragment on chromosome 11 and/or 12 (preferably in homozygous form, although not necessarily) and collecting the F1 hybrid seeds from said cross. The F1 hybrid may also comprise the introgression fragment on chromosome 11 and/or 12 in homozygous form, i.e. produced by crossing two inbred parent lines, each comprising the introgression fragment on chromosome 11 and/or 12 in homozygous or heterozygous form.

In a preferred aspect, the melon plant is an F1 hybrid and comprises the introgression fragment on chromosome 11 in homozygous form. Optionally, the F1 hybrid further comprises the introgression fragment on chromosome 12 in heterozygous or, preferably, in homozygous form. Such an F1 hybrid is preferably produced by crossing two inbred lines, each of which comprises the introgression fragment in chromosome 11 and the introgression fragment on chromosome 12, preferably both in homozygous form. Such inbred lines are also encompassed herein.

The melon plant according to the invention may be of any type. Preferably it has good agronomic and good fruit quality characteristics, such as e.g. large average fruit size (at least 500 g, 600 g, 700 g, 800 g, 900 g, 1000 g or more), high average brix of the fruits (e.g. an average refractometer % total soluble solids of at least 10%, 12%, 14%, 16%, 18% or more), many fruits being produced per plant, firm fruit flesh, etc.

The cultivated melon plants and plant cells belong in one aspect to one of the following species: *C. melo* var. *cantalupensis*, *C. melo* var. *inodorous* or *C. melo* var. *reticulatus*.

In one aspect the cultivated melon of the invention comprising one or two introgression fragments conferring ToLCNDV resistance, and the cultivated melon comprises one or more or all of the following characteristics: an average TSS at maturity of at least 10%, 11%, 12%, 13%, 14%, 15%, 16%, 17%, 18%; an attachment of the peduncle at fruit maturity which is not 'very weak' (UPOV characteristic 39 in TG/104/5 Rev., UPOV Code: CUCUM_MEL, found on the website UPOV.int); a shelf life of the fruit which is not 'very short' (UPOV characteristic 68 in TG/104/5 Rev., UPOV Code: CUCUM_MEL, found on the website UPOV.int); a fruit shape in longitudinal section which is not elongated (UPOV characteristic 28 in TG/104/5 Rev. UPOV Code: CUCUM_MEL, found on the website UPOV.int).

The average % TSS (or brix) can be measured as known in the art, e.g. using a digital hand refractometer and measuring the TSS of several mature fruits of a line or variety. See for example Burger et al. 2003, J American Soc Hort Science 128(4): 537-540 on page 538 at Measurement of TSS.

Also other resistances may be introduced into the melon plants of the invention, such as resistance to one or more of the following diseases: Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* fsp. *melonis* (Fom) race 0, *Fusarium oxysporum* fsp. *melonis* (Fom) race 1, *Fusarium oxysporum* fsp. *melonis* (Fom) race 2, *Fusarium oxysporum* fsp. *melonis* (Fom) race 1.2, *Fusarium* Wilt R2, Root Knot (Nematode), Anthracnose, Cucumber Mosaic, and Squash Mosaic, and/or resistance to one or more of the following pests: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced.

A specific aspect of the invention concerns plants or plant cells comprising an introgression fragment according to the invention which introgression fragment is obtainable from (derivable from, or as present in) seeds deposited under Accession number NCIMB 42625 or from progeny thereof. The seeds deposited are cultivated melon plants comprising both introgression fragments in homozygous form, with the donor nucleotide being present in homozygous form for SNP_01, SNP_02, SNP_03, SNP_04, SNP_05, SNP_06 and SNP_07. For the ToLCNDV resistance conferring QTL11 marker SNP_03 was found to be most significantly and for QTL12 SNP_06 was found to be most significant. This means that the size of the donor introgression can be reduced both for QTL11 and for QTL12, by selecting recombinants having smaller introgression fragment sizes for QTL11 and/or QTL12, i.e. sub-fragments of the fragments present in the deposited seeds. For example, plants comprising sub-fragments of these introgression fragments (wherein said sub-fragments still comprise the ToLCNDV resistance conferring QTL11 or 12), comprising the donor SNP genotype for SNP_03 (regarding QTL11) or comprising the donor SNP genotype SNP_06 (regarding QTL12), but having the SNP genotype of the recurrent parent for one or more or all of the other SNPs can be generated in ways known to the skilled person. Thus, melon plants comprising sub-fragments comprising only one of the donor SNPs (i.e. one of SNP_01, SNP_02, SNP_03 and SNP_04 for QTL11 and one of SNP_05, SNP_06 and SNP_07 for QTL12) but still retaining the resistance conferring QTL can be generated by the skilled person. It is even possible for the skilled person to remove all donor SNPs and still retain the QTL. One can sequence the chromosome 11 and/or 12 region to identify or determine if a plant has an introgression fragment or sub-fragment as present in (or obtainable from) seeds deposited under Accession number NCIMB 42625. Also, whether the QTL11 and/or 12 is still present on a sub-fragment which does not contain all of the donor SNPs or which even does not contain any of the donor SNPs anymore can be easily tested by carrying out a ToLCNDV resistance assay as described herein.

An introgression fragment can be identified by various methods, such as the polymorphic markers provided herein (SNP markers, polymorphic between the donor and the recurrent parent), chromosome painting or sequencing the melon genome and identifying the chromosome parts on chromosome 11 and/or 12 which are introgressions from a specific donor. The nucleotide sequence of the introgression fragment will be specific and unique for a donor accession that has been used to introgress the trait. For example to identify the introgression fragment from the specific donor of the invention e.g., whole genome sequencing of the genome of the seeds deposited can be done. This has, for example, also been done in tomato, where genome sequences of tomato inbreeding lines and hybrids identified introgression fragments on chromosome 6 and chromosome 9 of specific wild accessions. See Lin et al., Nature Genetics published Oct. 12, 2014, doi:10.1038/ng.3117, page 5, FIG. 4.

Apart from melon plants, also seeds from which such plants can be grown are provided herein.

A further aspect of the present invention, therefore, concerns melon seeds comprising an introgression fragment from chromosome 11 and/or 12 of a ToLCNDV resistant donor plant, wherein the introgression fragment comprises the sequence of the ToLCNDV resistant donor melon plant in-between SNP_01 and SNP_04, or in-between SNP_01 and SNP_03, or in-between SNP_01 and SNP_02, or in-between SNP_02 and SNP_04, or in-between SNP_02 and SNP_03, or in-between SNP_03 and SNP_04 for chromosome 11; and/or wherein the introgression fragment comprises the sequence of the ToLCNDV resistant donor melon plant in-between SNP_05 and SNP_07, or in-between SNP_05 and SNP_06, or in-between SNP_06 and SNP_07 for chromosome 12. It is understood that the introgression fragment comprises the resistance conferring QTL. Thus, if the introgression fragment is transferred into a ToLCNDV susceptible melon line or variety, especially in homozygous form, then the otherwise ToLCNDV susceptible line or variety will become resistant or highly resistant against ToLCNDV as described. In one aspect the cultivated melon plant comprising an introgression fragment comprising QTL11 and/or QTL12 has an average disease score of 9.0 (no symptoms), while the susceptible control shows the expected symptoms.

In another aspect ToLCNDV virus is not detected in the upper parts of the inoculated ToLCNDV resistant plants or is only detected at an extremely low level, see examples. Thus plants comprising QTL11 and/or QTL12 (e.g. a donor plant or a plant comprising one or both introgression fragments) comprise a significantly lower average ToLCNDV virus level (or virus titer) in the upper leaves at e.g. dpi (days post infection), 20 dpi, 25 dpi, 30 dpi and/or 35 dpi (or later) than the susceptible control line or variety. "Significantly lower" refers herein to an average virus level, detectable by e.g. qPCR, which is at least 1000 fold lower, more preferably at least 5000 fold, or at least 10000 fold, or at least 50000 fold, or at least 100000 fold, or at least 1000000 fold, lower than in the susceptible control tissue. Quantification of ToLCNDV levels is for example described in Simon et al. (Plant Disease January 2018, Volume 102, Number 1, Pages 165-171). In one aspect the average Ct (Cycle threshold) value of the resistant plant line is at least 2 times the value of the susceptible line or variety, or at least 2.5 times or 3.0 times the value. In one aspect the average Ct value of the resistant plant line is at least 30, 31, 32, 33, 34, 35, 36, 37 or 38, while the average Ct value of the susceptible line or variety is 15 or less, 14 or less, e.g. 13 or less, 12 or less, 11 or less, 10 or less. See e.g. world wide web at bitesizebio.com/24581/what-is-a-ct-value/or references cited therein. Ct-values are inverse to the amount of target nucleic acid (in this case ToLCNDV virus DNA) that is in a sample, and correlate to the number of copies in a sample. Lower Ct-values indicate high amounts of targeted nucleic acid, while higher Ct-values mean lower amounts of target nucleic acid.

In one embodiment of the invention the seeds comprise an introgression fragment from chromosome 11 of a ToLCNDV resistant donor plant, wherein the introgression fragment comprises the sequence of the ToLCNDV resistant donor melon plant in-between SNP_02 and SNP_04, or in-between SNP_02 and SNP_03, or in-between SNP_03 and SNP_04.

Another embodiment of the invention concerns melon seeds obtainable or obtained from plants according to the invention, or seeds comprising plant cells according to the invention.

A further aspect of the present invention concerns melon plant fruits comprising an introgression fragment from chromosome 11 and/or 12 of a ToLCNDV resistant donor plant, wherein the introgression fragment comprises the sequence of the ToLCNDV resistant donor melon plant in-between SNP_01 and SNP_04, or in-between SNP_01 and SNP_03, or in-between SNP_01 and SNP_02, or in-between SNP_02 and SNP_04, or in-between SNP_02 and SNP_03, or in-between SNP_03 and SNP_04 for chromosome 11; and/or wherein the introgression fragment comprises the sequence of the ToLCNDV resistant donor melon plant in-between SNP_05 and SNP_07, or in-between SNP_05 and SNP_06, or in-between SNP_06 and SNP_07 for chromosome 12.

Another embodiment of the invention concerns melon fruits obtainable or obtained from plants according to the invention, or fruits comprising plant cells according to the invention.

The preferred and further embodiments described herein for melon plant cells or melon plants according to the invention are applicable to also represent preferred and further embodiments of the melon fruits of melon plants according to the invention, accordingly.

A further aspect of the present invention concerns melon plant propagation material comprising an introgression fragment from chromosome 11 and/or 12 of a ToLCNDV resistant donor plant, wherein the introgression fragment comprises the sequence of the ToLCNDV resistant donor melon plant in-between SNP_01 and SNP_04, or in-between SNP_01 and SNP_03, or in-between SNP_01 and SNP_02, or in-between SNP_02 and SNP_04, or in-between SNP_02 and SNP_03, or in-between SNP_03 and SNP_04 for chromosome 11; and/or wherein the introgression fragment comprises the sequence of the ToLCNDV resistant donor melon plant in-between SNP_05 and SNP_07, or in-between SNP_05 and SNP_06, or in-between SNP_06 and SNP_07 for chromosome 12.

Another embodiment of the invention concerns melon plant propagation material obtainable or obtained from plants according to the invention, or melon plant propagation material comprising plant cells according to the invention.

The preferred and further embodiments described herein for plant cells or plants according to the invention are applicable to also represent preferred and further embodiments of the propagation material of melon plants according to the invention, accordingly.

The term "propagation material" comprises those components of the plant which are suitable for generating progeny via the vegetative (agamic) or generative (gamic, sexual) route. Suitable for vegetative propagation are, for example, cuttings, in vitro tissue, cell, protoplast, embryo or callus cultures, micropropagation methods, or roots. Other propagation material includes, for example, fruits, seeds, seedling, comprising the described one or two introgression fragments conferring ToLCNDV resistance etc. The propagation material in one aspect takes the form of cuttings which are propagated by grafting to another rootstock or in vitro tissue culture material, in particular embryo cultures. In particular preferred is propagation material in the form of in vitro tissue culture material, particularly in vitro embryo cultures.

A further embodiment of the invention concerns a method for producing a ToLCNDV resistant melon plant comprising the following steps
  a) Selecting a ToLCNDV resistant donor plant
  b) Crossing the donor plant selected in step a) with a recurrent plant sensitive to ToLCNDV
  c) Obtaining seeds from the plants crossed in step b) and optionally
  d) Selfing the plant grown from the seeds one or more time or backcrossing the plant grown from the seed to a recurrent plant sensitive to TolCNDV one or more times to obtain selfing or backcross progeny, and optionally
  e) Testing if (or testing which of) the plants grown from the seeds obtained in step c) or the selfing or backcross plants of step d) are resistant to ToLCNDV and/or if the plants comprise one or more of the SNPs from the donor plant selected from the group of SNP_01, SNP_02, SNP_03 and SNP_04; and/or SNP_05, SNP_06 and SNP_07.

The method optionally further comprises the step of selecting a ToLCNDV resistant plant comprising QTL11 and/or QTL12, preferably in homozygous form. Optionally the plant comprising one or more of the SNP markers is selfed to generate a homozygous plant.

A ToLCNDV resistant donor plant in step a) in the method for producing a ToLCNDV resistant melon plant according to the invention can be selected by infection of melon plants with ToLCNDV and determining the level of symptoms of ToLCNDV infected melon plants as described elsewhere herein. In one aspect the donor plant has an average disease score of 9.0. Optionally, the donor plant comprises one or more of the resistant SNP genotype for one or more or all of SNPs selected from SNP_01, SNP_02, SNP_03 and SNP_04; and/or for one or more or all of SNPs selected from SNP_05, SNP_06 and SNP_07. In one aspect the donor has an average disease score of 9.0 and comprises the resistant genotype of Table 3 for at least SNP_03 and/or SNP_06. In another aspect the donor has an average ToLCNDV disease score of 9.0 and comprises the resistant genotype for SNP_02, SNP_03 and SNP_04, optionally also for SNP_01. In a further aspect the donor has an average ToLCNDV disease score of 9.0 and comprises the resistant SNP genotype for SNP_01, SNP_02, SNP_03, SNP_04, SNP_05 and SNP_06, and optionally SNP_07. Preferably the donor is homozygous for the SNP genotypes. Optionally the donor may be selfed to select a donor plant which is homozygous. In a further aspect the donor plant comprises the same sequence in-between SNP_01 and SNP_04 and/or in-between SNP_05 and SNP_06 (optionally in-between SNP_05 and SNP_07) as the fragment introgressed in seeds deposited under accession number NCIMB 42625. The donor may be a wild melon or wild relative of melon. The donor may be the same donor as used to introgress QTL11 and QTL12 in seeds of NCIMB 42625. In one aspect ToLCNDV virus particles are very low (e.g. average Ct-value of at least 30 or more) or not detectable in the upper leaves of the donor plant following infection, e.g. using e.g. qPCR or dot blot as described e.g. in the Examples.

Another embodiment of the invention concerns a method for producing a ToLCNDV resistant melon plant comprising the following steps:
- a) Selecting a ToLCNDV resistant cultivated melon plant comprising an introgression fragment on chromosome 11 and/or 12, said introgression confers ToLCNDV resistance as described herein,
- b) Crossing the melon plant selected in step a) with another melon plant, e.g. a melon plant sensitive to ToLCNDV or a plant not resistant to ToLCNDV, e.g. a plant comprising an average TolCNDV disease score of 4.0 or less, preferably less than 4.0 or less than 3.0,
- c) Obtaining seeds from the plants crossed in step b) and optionally
- d) Selfing the plant grown from the seeds one or more time or backcrossing the plant grown from the seed to a plant sensitive to ToLCNDV one or more times to obtain selfing or backcross progeny, and optionally
- e) Testing if (or which of) the plants grown from the seeds obtained in step c) or the selfing or backcross plants of step d) are resistant to ToLCNDV and/or if the plants comprise one or more of the SNPs from the donor plant selected from the group of SNP_01, SNP_02, SNP_03 and SNP_04; and/or SNP_05, SNP_06 and SNP_07.

The method optionally further comprises the step of selecting a ToLCNDV resistant plant comprising QTL11 and/or QTL12, preferably in homozygous form.

A ToLCNDV resistant cultivated plant in step a) in the method for producing a ToLCNDV resistant melon plant according to the invention can be selected by infection of melon plants with ToLCNDV and determining the level of symptoms of ToLCNDV infected melon plants as described elsewhere herein. In one aspect the cultivated plant has an average disease score of at least 5.0, 6.0, 7.0, 8.0 or 9.0. Optionally, the cultivated plant comprises one or more of the resistant donor SNP genotypes for one or more or all of SNPs selected from SNP_01, SNP_02, SNP_03 and SNP_04; and/or for one or more or all of SNPs selected from SNP_05, SNP_06 and optionally SNP_07. In one aspect the cultivated plant is a cultivated melon plant comprising an introgression fragment on chromosome 11 and/or 12 as described throughout the specification. In one aspect the plant in step a) may be a plant grown from seeds deposited under accession number NCIMB 42625 or a progeny plant thereof which progeny plant retains QTL11 and/or QTL12. It may, thus, be a plant which comprises the same introgression fragment on chromosome 11 and/or 12 or a smaller introgression fragment on chromosome 11 and/or 12 than the one found in the deposited seeds.

In one aspect of the methods for producing a ToLCNDV resistant melon plant according to the invention the ToLCNDV resistant donor plant or cultivated melon plant in step a) comprises a fragment on chromosome 11 and/or 12 wherein the fragment comprises the sequence of the ToLCNDV resistant donor melon plant in-between SNP_01 and SNP_04, or in-between SNP_01 and SNP_03, or in-between SNP_01 and SNP_02, or in-between SNP_02 and SNP_04, or in-between SNP_02 and SNP_03, or in-between SNP_03 and SNP_04 for chromosome 11; and/or wherein the fragment comprises the sequence of the ToLCNDV resistant donor melon plant in-between SNP_05 and SNP_07, or in-between SNP_05 and SNP_06, or in-between SNP_06 and SNP_07 for chromosome 12.

In one embodiment of the invention the method for producing a ToLCNDV resistant melon plant according to the invention is used for producing a plant according to the invention. The preferred and further embodiments as described herein for the plants according to the invention are applicable accordingly to the method for producing a ToLCNDV resistant melon plant according to the invention.

Plants obtainable or obtained by a method for producing a ToLCNDV resistant melon plant according to the invention are also an embodiment of the invention.

A further embodiment of the invention concerns methods for producing melon fruits and optionally melon seeds comprising the following steps
- a) growing a ToLCNDV resistant melon plant comprising two chromosomes 11 each having an introgression fragment from chromosome 11 of a ToLCNDV resistant donor plant, the introgression fragment comprising the sequence of the donor plant for SNP_03, or in-between SNP_03 and SNP_04, or in-between SNP_02 and SNP_03; or the introgression fragment comprising the resistant donor genotype for one or more or all of SNP_01, SNP_02, SNP_03 and SNP_04;
- b) harvesting the fruits of the melon plants grown in step a), and optionally
- c) collecting the seeds from the fruits obtained in step b).

The melon plant of step a) is a plant as described in the specification, comprising QTL11 as described earlier, especially QTL11 is in homozygous form so that the phenotype is expressed. Optionally, the melon plant may further comprise an introgression fragment on chromosome 12, also as described earlier. Thus the plant of step a) may further comprise one or two chromosomes 12 having an introgression fragment on chromosome 12 of a ToLCNDV resistant donor plant, said introgression fragment comprising the sequence of the donor plant for SNP_05 and/or SNP_06 and/or SNP_07, or in-between SNP_05 and SNP_07, or in-between SNP_05 and SNP_06, or in-between SNP_06 and SNP_07.

In one aspect the cultivated melon plant of step a) is an F1 hybrid plant, and melon fruits for commercial use are produced.

In a preferred embodiment of the invention the melon plants of steps a) of the method for producing melon fruits or seeds according to the invention has the specific characteristics described as different embodiments of the plants according to the invention. The different embodiments as described herein for the plants according to the invention are applicable accordingly to the method for producing a hybrid melon seed according to the invention.

Seeds obtainable the method for producing melon seeds according to the invention are also an embodiment of the invention.

Another embodiment of the invention concerns methods for producing hybrid melon seeds, especially F1 hybrid seeds, comprising the following steps
- a) providing a first ToLCNDV resistant inbred melon plant comprising two chromosomes 11 each having an introgression fragment from chromosome 11 of a ToLCNDV resistant donor plant, the introgression fragment comprising QTL11 and the sequence of the donor plant for SNP_03, or in-between SNP_03 and SNP_04, or in-between SNP_02 and SNP_03; or the introgression fragment comprising QTL11 and the resistant donor genotype for one or more or all of SNP_01, SNP_02, SNP_03 and SNP_04;

b) providing a second ToLCNDV resistant inbred melon plant comprising two chromosomes 11 each having an introgression fragment from chromosome 11 of a ToLCNDV resistant donor plant, the introgression fragment comprising QTL11 and the sequence of the donor plant for SNP_03, or in-between SNP_03 and SNP_04, or in-between SNP_02 and SNP_03; or the introgression fragment comprising QTL11 and the resistant donor genotype for one or more or all of SNP_01, SNP_02, SNP_03 and SNP_04;

c) crossing the inbred melon plant provided in step a) with the inbred melon plant provided in step b)

d) collecting seeds obtained from the cross of step c).

In one aspect the inbred plant of step a) or of step b) is male sterile, so that only cross pollination occurs in step c), generating F1 hybrid seeds in step d).

Optionally the inbred plant in step a) or in step b) comprises in addition two chromosomes 12, each of which comprises an introgression fragment having QTL12, as described. Thus in one aspect the plant in step a) or in step b) comprises QTL11 in homozygous form and further comprises QTL12 homozygous form. The F1 hybrid seeds therefore comprise QTL11 in homozygous form and QTL12 in heterozygous form.

In another aspect both the plant in step a) and the plant in step b) comprise QTL11 in homozygous form and QTL12 in homozygous form. The F1 hybrid seeds of step c) therefore comprise both QTLs in homozygous form.

The hybrid seed, especially F1 hybrid seed, collected are also an embodiment of the invention. These are the seeds that are sold for commercial melon fruit production. Plants grown from these seeds will be resistant or highly resistant against ToLCNDV in the fruit production fields.

In a different embodiment of the invention concerns methods for producing hybrid melon seeds, especially F1 hybrid seeds, comprising the following steps a) providing a first ToLCNDV resistant inbred melon plant comprising two chromosomes 12 each having an introgression fragment from chromosome 12 of a ToLCNDV resistant donor plant, the introgression fragment comprising QTL12 and the sequence of the donor plant for SNP_06, or in-between SNP_05 and SNP_07, or in-between SNP_05 and SNP_06, or in-between SNP_06 and SNP_07; or the introgression fragment comprising QTL12 and the resistant donor genotype for one or more or all of SNP_05 and SNP_06 and SNP_07;

b) providing a second inbred melon plant;

c) crossing the inbred melon plant provided in step a) with the inbred melon plant provided in step b)

d) collecting seeds obtained from the cross of step c).

Optionally the second inbred melon plant in step b) is also a ToLCNDV resistant inbred melon plant comprising two chromosomes 12 having an introgression fragment from chromosome 12 of a ToLCNDV resistant donor plant, the introgression fragment comprising QTL12 and the sequence of the donor plant for SNP_06, or in-between SNP_05 and SNP_07 or in-between SNP_05 and SNP_06, or in-between SNP_06 and SNP_07; or the introgression fragment comprising QTL12 and the resistant donor genotype for one or more or all of SNP_05 and SNP_06 and SNP_07.

In one aspect the inbred plant of step a) or of step b) is male sterile, so that only cross pollination occurs in step c), generating F1 hybrid seeds in step d).

The F1 hybrid seeds collected in step d) comprise QTL12 in either heterozygous form or in homozygous form. As QTL12 is partially dominant, the ToLCNDV resistance score will be slightly higher in the homozygous plant than in the plant heterozygous for QTL12.

The hybrid seed, especially F1 hybrid seed, collected are also an embodiment of the invention. These are the seeds that are sold for commercial melon fruit production. Plants grown from these seeds will be resistant against ToLCNDV in the fruit production fields.

"Inbred plant" or "inbred line" shall mean in connection with the present invention plants which have undergone several generations of selfing and are highly uniform in respect to their genetic setup and phenotypic appearance.

In a preferred embodiment of the invention the inbred lines of steps a) and b) of the method for producing hybrid melon seeds according to the invention has the specific characteristics described as preferred and further embodiments of the plants according to the invention. The preferred and further embodiments as described herein for the plants according to the invention are applicable accordingly to the method for producing a hybrid melon seed according to the invention.

Hybrid seeds obtainable or obtained by the method for producing hybrid melon seeds according to the invention are also an embodiment of the invention.

A further embodiment of the present invention are methods for producing a melon fruit comprising the following step a) growing a F1 hybrid plant described above, i.e. comprising QTL11 in homozygous form and/or QTL12 in heterozygous or homozygous form in its genome, and optionally b) harvesting the fruits produced by the plants grown in step a).

The term "fruit" in its botanical meaning is commonly understood to be a seed bearing structure developed from the ovary of angiosperm flowers.

Melon fruits obtainable or obtained by a method for producing a melon fruit according to the invention are also an embodiment of the invention.

Melon donor plants being resistant to ToLCNDV due to the presence of QTL11 and/or QTL12 in their genome can be identified with the aid of the SNP markers, in particular one or more or all of SNP_01, SNP_02 SNP_03, SNP_04 and/or one or more of SNP_05, SNP_06 and SNP_07 disclosed herein. The present invention therefore for the first time enables a person skilled in the art to identify donor plants from which an introgression fragment conferring ToLCNDV resistance to melon plants can be transferred into recurrent melon plants.

Likewise, the invention provides for the first time cultivated melon plants, plant parts and cells, comprising in their genome an introgression fragment on chromosome 11 and/or 12, which confers ToLCNDV resistance to an otherwise susceptible melon plant.

A further embodiment of the invention therefore pertains the use of one or more or all of SNP_01, SNP_02, SNP_03, SNP_04 and/or one or more or all of SNP_05, SNP_06 and SNP_07 for identification of a ToLCNDV resistant melon plant or parts thereof (such as cells, fruits, leaves).

Preferably the use pertains to the identification of a ToLCNDV resistant donor melon plant or plant part and/or a cultivated melon plant or plant part.

Another embodiment is the use of one or more or all of SNP_01, SNP_02, SNP_03, SNP_04 and/or of one or more or all of SNP_05, SNP_06 and SNP_07 for introgression of ToLCNDV resistance into a ToLCNDV susceptible melon plant, especially a cultivated melon line or variety.

Also an embodiment of the invention is the use of one or more or all of SNP_01, SNP_02, SNP_03, SNP_04 and/or one or more or all of SNP_05, SNP_06 and SNP_07 in breeding ToLCNDV resistant melon plants.

Also provided is a method of screening (or selecting) plants or plant parts (such as plant tissues, cells, etc.) or DNA derived therefrom for the presence of a fragment on chromosome 11 and/or 12 conferring ToLCNDV resistance. The method comprises the steps of:
  i) screening the genomic DNA for the SNP genotype of one or more or all of SNP_01, SNP_02, SNP_03, SNP_04 and/or one or more or all of SNP_05, SNP_06 and SNP_07;
  ii) and optionally selecting a plant or plant part which comprise the resistant donor genotype of one or more or all of SNP_01, SNP_02, SNP_03, SNP_04 and/or for one or more or all of SNP_05, SNP_06 and SNP_07.

Such screening can be carried out using various methods, such as SNP genotyping assays (e.g. KASP assays, TaqMan assays, a High Resolution Melting (HRM) assays, SNP-genotyping arrays such as e.g. Fluidigm, Illumina, etc., or DNA sequencing may equally be used.

As clear throughout the description, screening of plants, plant parts, or genomic DNA thereof, can be used for various purposes, for example identification of ToLCNDV resistant donors, or as part of a breeding program, e.g. identification and/or selection of plants or plant parts comprising QTL11 and/or QTL12, or for checking whether competitors are making use of the instant invention and produce inbred lines or hybrids comprising QTL11 and/or QTL12.

Also provided is a method for growing the plants of the invention, e.g. in areas where ToLCNDV virus infestation occurs, comprising sowing the seeds or planting seedlings into a growing area (e.g. a field or protected environment such as a glasshouse or tunnel) and optionally harvesting the fruits.

Cells or tissues comprising an introgression fragment on chromosome 11 and/or 12 as described herein may consist of or comprise non-propagating cells or tissues, or non-regenerable cells or tissues, or alternatively propagating or regenerable cells or tissues. They may comprise or consist of photosynthetic or non-photosynthetic cells. Vegetative plant parts, cells and tissues, such as harvested fruits or fruit flesh parts are non-photosynthetic parts and tissues. Cells and tissues may be in cell or tissue cultures.

Harvested fruits or processed fruits are also encompassed herein, e.g. slices, blocks or cubes of melon fruit flesh, e.g. in a container.

In one aspect the plants, plant parts and plant cells according to the invention are not exclusively obtained by means of an essentially biological process as defined by Rule 28 (2) EPC (European Patent Convention).

In one aspect the plants are non-GMO (not genetically modified).

The instant QTL11 is a different QTL than the one described in WO2017/114848, as the location on chromosome 11 is a different location. This is evident when BLAST-ing the sequences of SNP_1 to SNP_16 markers against the CM3.6.1 genome of melon. The most closely linked markers are Melon_sbg_33761_74 (SEQ ID NO: 7), Melon_sbg_2720_78 (SEQ ID NO: 8) and Melon_sbg_14207_58 (SEQ ID NO: 9), which are located at 33.18 Mb, 33.34 Mb and 33.35 Mb of the chromosome. In contrast, the most closely linked marker of the instant QTL11, SNP_03, is located at 32.49 Mb. This location is further upwards on chromosome 11, in the region of their marker Melon_sbg_55680_17 (SEQ ID NO: 5), located at 32.3 Mb, and Melon_sbg_60684_74 (SEQ ID O: 6) located at 32.6 Mb. However, in RIL-30 the introgression fragment is not present in the region corresponding to Melon_sbg_617_42 (SEQ ID NO: 1) to Melon_sbg_33761_74 (SEQ ID NO: 7), while the line is still resistant to ToLCNDV and still contains their QTL11. The nucleotide sequence of their introgressions will also be entirely different than the nucleotide sequence of the instant invention, as the donor is a *Cucumis melo* subsp. *agrestis* var acidulous accession, while the instant donor is a *Cucumis melo* subsp. *melo* accession. *Cucumis melo* subsp. *agrestis* is phylogenetically in a separate cluster from *Cucumis melo* subsp. *melo*, see for example Supplementary Figure S3 of Gur et al. "Genome-Wide Linkage-Disequilibrium Mapping to the Candidate Gene Level in Melon (*Cucumis melo*)", Scientific Reports, volume 7, Article number: 9770 (2017), doi:10.1038/s41598-017-09987-4.

Seed Deposit Information

A representative sample of seeds of a cultivated melon, designated *Cucumis melo* TOLCHR11-12, comprising two introgression fragments (in homozygous form), one comprising ToLCNDV resistance introgressed on chromosome 11 and one comprising ToLCNDV resistance introgressed on chromosome 12, was deposited by Nunhems B.V. on 10 Aug. 2016 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers NCIMB 42625.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Description of Sequences

Characters other than G (guanine), A (adenine), T (thymine) and C (cytosine) have the following meaning in the SEQ ID NOs shown in the sequence listing:

R: G or A

Y: T or C

M: A or C

K: G or T

S: G or C

W: A or T

H: A or C or T

-continued

B: G or T or C

V: G or C or A

D: G or A or T

N: G or A or T or C

SEQ ID NO 1:
Sequence of the ToLCNDV resistant donor plant comprising SNP_01.

SEQ ID NO 2:
Sequence of the ToLCNDV resistant donor plant comprising SNP_02.

SEQ ID NO 3:
Sequence of the ToLCNDV resistant donor plant comprising SNP_03.

SEQ ID NO 4:
Sequence of the ToLCNDV resistant donor plant comprising SNP_04.

SEQ ID NO 5:
Sequence of the ToLCNDV resistant donor plant comprising SNP_05.

SEQ ID NO 6:
Sequence of the ToLCNDV resistant donor plant comprising SNP_06.

SEQ ID NO 7:
Sequence of the ToLCNDV resistant donor plant comprising SNP_07.

SEQ ID NO 8-10:
SNP_01 FAM Allele Primer, SNP_01 VIC allele primer, SNP_01 Common Primer SEQ ID NO 11-13:
SNP_02 FAM Allele Primer, SNP_02 VIC allele primer, SNP_02 Common Primer SEQ ID NO 14-16:
SNP_03 FAM Allele Primer, SNP_03 VIC allele primer, SNP_03 Common Primer SEQ ID NO 17-19:
SNP_04 FAM Allele Primer, SNP_04 VIC allele primer, SNP_04 Common Primer SEQ ID NO 20-22:
SNP_05 FAM Allele Primer, SNP_05 VIC allele primer, SNP_05 Common Primer SEQ ID NO 23-25:
SNP_06 FAM Allele Primer, SNP_06 VIC allele primer, SNP_06 Common Primer SEQ ID NO 26-28:
SNP_07 FAM Allele Primer, SNP_07 VIC allele primer, SNP_07 Common Primer

```
                                              SEQ ID NO: 1
gctaatgaac tcgggttttg aaacgctcag aggattatcg ttaccggaaa catgaacgga agtccatgtt ttgacaaacg aactaatgga cgacgcgtcg aaaatcttgt gcgacatgag taagccaaca gtaatgcctc cacattgaaa cgtcgtggtt tggatgagta caatacatcc tttgttagcg agatgaaaag g SEQ ID NO: 2
gtttgttttg atcaaaaaaa tcaaacattt aagtaaataa tatactacat taaatgtgta agtgagtcta gcagtataca ttccgtcgat gtactaaact gaattcaaag agtttatgca tataagtgaa tgaatatccc aaaacttatc aatttcagaa gaagagaaaa aactaggttt ccttatcctt tttgtgagcc a SEQ ID NO: 3
ctcgtagagc atttgaacgc cacagtggaa ctggccgtgg gtaagtgtct gctgtctgtt cttttaaatt ttgttgtgca cactcctgct gcatattcta tgccattttg acacttcatt cctgatttta tgcctagaaa tgaatttaaa cgagaagggt ctggtcgtgg aaattgggga aggtcaactg acgaatttgc t SEQ ID NO: 4
tctctctggt ggataactca tgtaatggtc ttgtctttat ttgtaagtgt gctttttta ctcgttgtga tggcatattc aatcctatga ctaatgagtt tttccaaatt cctcgaggtg aattagatgg tgatatttac tcctacgaat taggttttag ccctacaaca aagcaataca aattgtttcg agttaccgaa t SEQ ID NO: 5
atacaaccca tcaaccaaaa tcttccaact aattatagag actttgataa aaggaaaaaa aagagtaaca aatagcgatg cgaggaaagg gacgatggcc cgtacatatt agcatgctca taaacaaatt caaaaagccc aacaaagacg aagaaaaata acgaaaacca tgatggcaca aagcattgtc aagtctcgga a SEQ ID NO: 6
tgacaacagc tttcaccacc aatcaataaa atgaggatgg attcaagatt tatgccaaca ccctgatccc aaattgaaga tgccaaacaa agggacacag gaatcattgt ctaagaaatt gtaaaaaccc cacaatgaaa acttctatca aagacacggg aatctacagt ttgtacagtc acttgcacaa gcatcttcaa a SEQ ID NO: 7
atcgttataa agtcgtcaat ggcatgacgc acaatcggtc cttcaaccat tgtaaaacca acgtcgaatt tgcataacgt gtcgtcctca acatgattag tgacacgata agcgacaaaa atttcgggaa aatttagttg ttgatcctca acatcgtcca cttcgggtac gtttcatata cgtttatttt ggacaaccta a
```

DESCRIPTION OF THE FIGURES

FIG. 1: Shown are the average symptom levels (of three replicates) at 35 days post infection (dpi) with ToLCNDV by whitefly transmission of a donor plant line being ToLCNDV resistant (Wild Donor), a recurrent plant line (Recurrent) and of plant line NCIMB 42625. The average symptom levels were determined as described herein under "General Methods".

GENERAL METHODS

1. Determination of Symptom Level on ToLCNDV Infected Plants 1.1 Plants and Pathogens (Virus)

A melon plant (*Cucumis melo*) infecting strain of ToLCNDV was used for infection of melon plants. In the present invention a ToLCNDV strain isolated in Murcia, Spain was used as inoculum.

1.2 ToLCNDV Inoculum

The ToLCNDV inoculum source was maintained on living infected melon plants. It must be ensured, that pure virus isolates are used and that neither the virus source, nor the whiteflies are contaminated with other diseases, in particular with other viruses (e.g. CGMMV, CYSDV, CYVY, SqMV). For pre-multiplication of the ToLCNDV inoculum whiteflies (*Bemisia tabaci*) were fed on ToLCNDV sensitive (susceptible), infected melon plants in an insect proof cage. Before infection of test plants, the ToLCNDV infected plants were placed into an insect proof cage, whiteflies were released into the same cage and allowed to feed for approximately 3 days on the ToLCNDV infected plants.

1.3 Inoculation of Plants to be Tested

For each genotype of melon plants to be analysed 14 plants were grown until the first true leaf is expanded (normally 12-15 days after sowing), 12 of which were infected and 2 were mock infected. Also 12 plants of susceptible varieties were included, in this experiment variety Gandalf F1 (Hild Samen) and variety Vedantrais. The 12 plants per genotype to be tested for ToLCNDV resistance were placed into an insect proof cage, infected whiteflies (obtained as described under 1.2 above) were released into the cage to infect the plants. It has to be ensured that at least 5-10 whiteflies are available for each test plant in the cage. Whiteflies and test plants are kept in the cage for approximately 48 hours, then the whiteflies are eliminated with an appropriate insecticide. Also two plants per genotype were mock infected, i.e. they were treated in the same manner as the test plants apart from the fact that the whiteflies used for infection were free of ToLCNDV.

1.4 Growing Infected Test Plants

Infected test plants obtained as described under 1.3 were transplanted to bigger pots, transferred into a greenhouse with cooling equipment. The plants were grown at approximately 18° C. night temperature and approximately 25° C. day temperature in a timeframe of 14 to 16 hours daylight. The infected plants for each infected genotype were grown in two replicates in two different plots, each of which comprised 6 ToLCNDV infected plants and 1 mock infected plant. The plots are randomized in respect to the growing area.

1.5. Scoring the Symptom Level of ToLCNDV Infection

The scoring of the symptom level may already be done approximately 15 days post infection (dpi) with ToLCNDV but is preferably done approximately 30 days post infection (dpi) with ToLCNDV, or later, e.g. 35 dpi. In case plants are present which show recovery from the virus infection, a further scoring of the symptom can optionally be done approximately 45 days post infection (dpi) with ToLCNDV.

The following symptom levels are to be used according to the phenotypes indicated in the following:

| Symptom level | Observed phenotype |
| --- | --- |
| 1 | Dead plant |
| 2 | Severe mosaic and curling, chlorosis and growth reduction. No recovery |
| 3 | Strong mosaic and curling, chlorosis and growth reduction. No recovery |
| 4 | Curling and mosaic, chlorosis, no or mild growth reduction. No recovery |
| 5 | Curling and mosaic, chlorosis, no growth reduction. Slight recovery of the upper plant zone |
| 6 | Mild curling, mosaic and chlorosis, no growth reduction. Recovery of the upper middle plant |
| 7 | Mild curling, mosaic and chlorosis, no growth reduction. Symptoms appear only in the lower plant zone |
| 8 | Faint mosaic |
| 9 | No symptoms |

1.6 Optional Additional Tests

It is recommended to use at least one genotype highly resistant to ToLCNDV (e.g. average symptom level 8-9) and/or one genotype highly sensitive to ToLCNDV (e.g. average symptom level 1 or 2) in each experimental setup as controls. It is further recommended to also include a genotype having intermediate resistance to ToLCNDV infection in each test setup. When these control genotypes show the expected symptom level, this gives a clear indication that the experimental conditions are right to evaluate the test plants. It is especially important to include a susceptible control line or variety, which shows the expected symptoms at the time of scoring, e.g. 30 dpi or later (e.g. 35 dpi).

Furthermore, it is advisable to check infection and spreading of ToLCNDV in infected plants and control plants. This can be done by checking for the presence and/or amount of virus DNA in upper parts of the plants. A suitable way to check for the presence and/or amount of ToLCNDV DNA in upper plant parts is hybridization of plant material with a probe hybridizing with the DNA of the ToLCNDV strain used. Various hybridization techniques are well known in the art. A simple so called Dot Blot analysis is sufficient for obtaining valuable results. Additionally or alternatively qPCR can be used.

1. Selection of ToLCNDV Resistant Donor Plants

The symptom level of wild accessions of melon plants were tested for ToLCNDV resistance according to the test described under "General Methods". A wild donor plant was identified which has a high resistance to ToLCNDV infection, having an average disease score of 9 (no symptoms) at 15 dpi, 25 dpi and 35 dpi, while the susceptible control line had an average disease score of 2.8 at 15 dpi, 2.0 at 25 dpi and 2.0 at 35 dpi.

Also—blot hybridization and qPCR (quantitative PCR) were carried out on infected donor plants and a susceptible control line after 30 dpi. No ToLCNDV virus was detected in the donor tissue at 30 dpi, while ToLCNDV virus was detected in the susceptible control. (Note that a low Ct-value indicates a high virus titer, while a high Ct-value indicates a low amount of virus)

|  | Dot-blot signal | qPCR- average Ct value | ng/µl |
| --- | --- | --- | --- |
| Donor line | − | 33.8 | 3.76E−07 |
| Susceptible line | + | 13.1 | 0.19 | qPCR negative control Ct = 34

Another real time qPCR (quantitative PCR) experiment was carried out, using a protocol described in Simon et al. 2018 (supra). In short, the primers and probes ToLA-up (forward primer), ToLA-Low (reverse primer) and ToLA-Probe (TaqMan probe) of Table 1 of Simon et al 2018

(supra) were used in a qPCR analysis as described therein, with thermos cycling conditions being incubation at 95° C. for 2 minutes followed by 40 cycles of 95° C. for 15 seconds and 60° C. for 1 minute.

Plants of the donor and of the susceptible variety Vedantrais were sown and inoculated with ToLCNDV as described herein above. Three replicates of six plants per genotype were used and three mock inoculated Vedantrais plants were included per replicate. Phenotypic scoring of each plant was done at dpi, 30 dpi and 45 dpi. Samples for qPCR were taken at 60 dpi from each plant.

| Genotype | Average ToLCNDV disease score | STDV | Average Ct-value (60 dpi) | STDV |
|---|---|---|---|---|
| Donor line | 9.0 | 0.0 | 30.59 | 3.12 |
| Susceptible line (Vedantrais) | 2.75 | 0.49 | 10.07 | 1.32 |
| Mock inoculated susceptible line (Vedantrais) | 9.0 | 0.0 | 39.97 | 0.42 |

STDV = standard deviation

Results confirmed that the symptom free donor line had extremely low ToLCNDV virus levels in the leaves at 60 dpi.

2. Identification of Genomic Location of ToLCNDV Resistance

Three mapping populations were developed using the donor plant obtained in Example 1 to map the position of the ToLCNDV resistance conferring loci (QTL). Phenotyping of the mapping populations was carried out as described above, using a TolCNDV scale of 1 to 9. Genotyping was initially carried out using 192 SNP markers, and later additional SNP markers were run to saturate the QTL regions.

Analysis in these mapping populations revealed two major QTLs associated with resistance, located on chromosome 11 and 12.

From resistant material the inventors developed backcross lines to fine map and further investigate resistance from the donor.

The markers identified during fine mapping and their respective positions according to publicly known data from Diaz et al. (2015, Mol Breeding 35, 188) is shown in Table 2 (in the description).

3. Development of KASP-Assays

A KASP-assay was developed for identifying the SNPs linked to QTL11 (SNP_01, SNP_02, SNP_03 and SNP_04) and QTL12 (SNP_05, SNP_06 and SNP_07). The SNPs associated with QTL11 and QTL12 can be determined by use of the following primers in a KASP-assay:

| SNP | FAM allele | VIC allele | Common Primer |
|---|---|---|---|
| SNP_01 | SEQ ID NO 8 | SEQ ID NO 9 | SEQ ID NO 10 |
| SNP_02 | SEQ ID NO 11 | SEQ ID NO 12 | SEQ ID NO 13 |
| SNP_03 | SEQ ID NO 14 | SEQ ID NO 15 | SEQ ID NO 16 |
| SNP_04 | SEQ ID NO 17 | SEQ ID NO 18 | SEQ ID NO 19 |
| SNP_05 | SEQ ID NO 20 | SEQ ID NO 21 | SEQ ID NO 21 |
| SNP_06 | SEQ ID NO 23 | SEQ ID NO 24 | SEQ ID NO 25 |
| SNP_07 | SEQ ID NO 26 | SEQ ID NO 27 | SEQ ID NO 28 |

4. Introgression of ToLCNDV into a Cultivated Melon Plant

Backcrossing was performed with a recurrent parent elite breeding line of a Piel de Sapo type to develop a line comprising both QTL11 and QTL12 in homozygous form.

Seeds of an introgression line comprising both QTL11 and QTL12 in homozygous form were deposited under NCIMB 42625. The donor genotype is present for SNP_01 to SNP_04 and for SNP_05 to SNP_07, as verified using the KASP assay.

FIG. 1 and the Table below shows that the donor and the introgression line deposited have an average disease score of 9.0 when scored 35 dpi, while the susceptible recurrent parent line has an average disease score of 2.4 at 35 dpi.

| | AVG | STDV |
|---|---|---|
| Wild Donor | 9.0 | 0.0 |
| Recurrent (susceptible) parent | 2.4 | 0.43 |
| NCIMB 42625 (melon plant comprising introgression fragment on chr. 11 and chr. 12) | 9.0 | 0.0 |

AVG: average value of tested genotype, STDV: standard deviation

Additional backcrossing was done with the donor to introgress one or both QTLs into elite Galia, Cantaloupe and Charentais backgrounds.

The invention claimed is:

1. A cultivated melon plant or plant cell comprising an introgression fragment from chromosome 12 of a ToLCNDV resistant donor plant, wherein the introgression fragment on chromosome 12 comprises a sequence of the ToLCNDV resistant donor melon plant in-between SNP_05 at nucleotide 101 of SEQ ID NO: 5 and SNP_07 at nucleotide 101 of SEQ ID NO: 7, and wherein the introgression fragment comprises a Guanine for SNP_06 at nucleotide 101 of SEQ ID NO: 6, and wherein the introgression fragment on chromosome 12 is obtainable from seeds deposited under accession number NCIMB 42625.

2. The cultivated melon plant or plant cell according to claim 1, wherein the introgression fragment on chromosome 12 further comprises a Cytosine at nucleotide 101 of SEQ ID NO: 5 and/or a Thymine at nucleotide 101 of SEQ ID NO: 7.

3. A cultivated melon plant or plant cell according to claim 1, wherein the introgression fragment on chromosome 12 comprises a Cytosine at nucleotide 101 of SEQ ID NO: 5 or of a sequence comprising at least 90% sequence identity to SEQ ID NO: 5, and a Guanine at nucleotide 101 of SEQ ID NO: 6 or of a sequence comprising at least 90% sequence identity to SEQ ID NO: 6 and a Thymine at nucleotide 101 of SEQ ID NO: 7 or of a sequence comprising at least 90% sequence identity to SEQ ID NO: 7.

4. The cultivated melon plant or plant cell according to claim 1, wherein the introgression fragment on chromosome 12 is in homozygous form.

5. The cultivated melon plant or plant cell according to claim 1, wherein the introgression fragment on chromosome 12 is from a wild melon or wild relative of melon.

6. The cultivated melon plant or plant cell according to claim 1, wherein the introgression fragment on chromosome 12 comprises a partially dominant QTL which confers an average TolCNDV resistance score of at least 5 on a scale of 1 (dead plant) to 9 (no symptoms) when the QTL is in homozygous form.

7. The cultivated melon plant or plant cell according to claim 1, wherein the plant or plant cell is an inbred plant or plant cell or an F1 hybrid plant or plant cell.

8. A seed which grows into a plant according to claim 1.

9. A cultivated melon fruit or fruit part comprising plant cells according to claim 1.

10. A cultivated melon plant propagation material comprising a cultivated melon plant cell according to claim 1.

11. A method of crossing an inbred line according to claim 7 to another inbred line and collecting the F1 hybrid seed produced from said cross.

12. A method for producing hybrid cultivated melon seeds comprising the following steps
  a) providing a first ToLCNDV resistant inbred melon plant comprising two chromosomes 12 each having an introgression fragment from chromosome 12 of a ToLCNDV resistant donor plant, the introgression fragment comprising QTL12 and a Guanine at nucleotide 101 of SEQ ID NO: 6 for SNP_06; or the introgression fragment comprising QTL12 and the resistant donor genotype for one or more or all of SNP_05 at nucleotide 101 of SEQ ID NO: 5, SNP_06 at nucleotide 101 of SEQ ID NO: 6 and/or SNP_07 at nucleotide 101 of SEQ ID NO: 7;
  b) providing a second inbred melon plant;
  c) crossing the inbred melon plant provided in step a) with the inbred melon plant provided in step b); and
  d) collecting seeds obtained from the cross of step c).

13. A method of screening plants or plant parts, or DNA derived therefrom, for the presence of a fragment on chromosome 12 conferring ToLCNDV resistance comprises the steps of:
  i) screening the genomic DNA for the SNP genotype of one or more or all of SNP_05 at nucleotide 101 of SEQ ID NO: 5, SNP_06 at nucleotide 101 of SEQ ID NO: 6 and/or SNP_07 at nucleotide 101 of SEQ ID NO: 7;
  ii) and optionally selecting a plant or plant part comprising a Cytosine at nucleotide 101 of SEQ ID NO: 5 and/or a Guanine at nucleotide 101 of SEQ ID NO: 6 and/or a Thymine at nucleotide 101 of SEQ ID NO: 7.

14. The method according to claim 12, wherein the second inbred melon plant of step b) comprises two chromosomes 12 each having an introgression fragment from chromosome 12 of a ToLCNDV resistant donor plant, the introgression fragment comprising QTL12 and a Guanine at nucleotide 101 of SEQ ID NO: 6 for SNP_06; or the introgression fragment comprising QTL12 and the resistant donor genotype for one or more or all of SNP_05 at nucleotide 101 of SEQ ID NO: 5, SNP_06 at nucleotide 101 of SEQ ID NO: 6 and/or SNP_07 at nucleotide 101 of SEQ ID NO: 7.

* * * * *